US011951272B2

(12) United States Patent
Xu et al.

(10) Patent No.: US 11,951,272 B2
(45) Date of Patent: Apr. 9, 2024

(54) CRYO FORMULATION-BASED MICRONEEDLE DEVICE FOR OCULAR DELIVERY OF BIOACTIVE THERAPEUTIC AGENTS USING A CRYO-MICRONEEDLE PATCH

(71) Applicant: City University of Hong Kong, Kowloon (HK)

(72) Inventors: Chenjie Xu, Kowloon (HK); Hao Chang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 268 days.

(21) Appl. No.: 17/443,523

(22) Filed: Jul. 27, 2021

(65) Prior Publication Data

US 2023/0038697 A1    Feb. 9, 2023
US 2023/0270984 A9    Aug. 31, 2023

Related U.S. Application Data

(60) Provisional application No. 63/071,491, filed on Aug. 28, 2020.

(51) Int. Cl.
A61M 37/00 (2006.01)

(52) U.S. Cl.
CPC . *A61M 37/0015* (2013.01); *A61M 2037/0023* (2013.01); *A61M 2037/0053* (2013.01);
(Continued)

(58) Field of Classification Search
CPC ...... A61M 37/0015; A61M 2037/0023; A61M 2037/0053; A61M 2037/0061;
(Continued)

(56) References Cited

U.S. PATENT DOCUMENTS

2002/0091357 A1* 7/2002 Trautman ............. A61B 17/205
    606/186
2010/0114348 A1* 5/2010 Boyden ................. G16H 50/50
    700/109
(Continued)

FOREIGN PATENT DOCUMENTS

WO    2015132568    9/2015

OTHER PUBLICATIONS

Jian, H.-J.; Wu, R.- S.; Lin, T.-Y.; Li, Y.-J.; Lin, H.-J.; Harroun, S. G.; Lai, J.-Y.; Huang, C.-C., Super-Cationic Carbon Quantum Dots Synthesized from Spermidine as an Eye Drop Formulation for Topical Treatment of Bacterial Keratitis. Acs Nano 2017, 11 (7), 6703-6716.

(Continued)

*Primary Examiner* — Amber R Stiles
(74) *Attorney, Agent, or Firm* — Renner, Kenner, Greive, Bobak, Taylor & Weber

(57) ABSTRACT

A cryo formulation-based microneedle device for ocular delivery of bioactive therapeutic agents. The microneedle device includes: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on cornea of an eye, in which the miniaturized needles penetrates into the eye; and wherein the miniaturized needles is further arranged to melt so as to release one or more bioactive therapeutic agents into the eye to achieve a targeted therapeutic effect.

38 Claims, 28 Drawing Sheets
(1 of 28 Drawing Sheet(s) Filed in Color)

(52) U.S. Cl.
CPC . *A61M 2037/0061* (2013.01); *A61M 2202/03* (2013.01); *A61M 2202/07* (2013.01); *A61M 2202/203* (2013.01); *A61M 2202/206* (2013.01); *A61M 2202/30* (2013.01); *A61M 2210/0612* (2013.01)

(58) Field of Classification Search
CPC .......... A61M 2202/03; A61M 2202/07; A61M 2202/203; A61M 2202/206; A61M 2202/30; A61M 2210/0612; A61M 2037/0046; A61B 18/02; A61B 18/0218; A61B 2018/00321; A61B 2018/0293; A61F 9/00; A61F 9/007
See application file for complete search history.

(56) References Cited

U.S. PATENT DOCUMENTS

| | | | |
|---|---|---|---|
| 2016/0158511 A1* | 6/2016 | Jin | A61K 9/0021 264/28 |
| 2017/0050010 A1* | 2/2017 | McAllister | B33Y 80/00 |
| 2019/0046479 A1* | 2/2019 | Pathak | A61K 9/1641 |
| 2022/0062606 A1* | 3/2022 | Chen | B29C 39/026 |
| 2023/0033564 A1* | 2/2023 | Xu | A61K 9/0021 |

OTHER PUBLICATIONS

Laxminarayan, R.; Duse, A.; Wattal, C.; Zaidi, A. K.; Wertheim, H. F.; Sumpradit, N.; Vlieghe, E.; Hara, G. L.; Gould, I. M.; Goossens, H.; Greko, C.; So, A. D.; Bigdeli, M.; Tomson, G.; Woodhouse, W.; Ombaka, E.; Peralta, A. Q.; Qamar, F. N.; Mir, F.; Kariuki, S.; Bhutta, Z. A.; Coates, A.; Bergstrom, R.; Wright, G. D.; Brown, E. D.; Cars, O., Antibiotic resistance-the need for global solutions. Lancet Infect Dis 2013, 13 (12), 1057-98.

Shatzkes, K.; Singleton, E.; Tang, C.; Zuena, M.; Shukla, S.; Gupta, S.; Dharani, S.; Onyile, O.; Rinaggio, J.; Connell, N. D.; Kadouri, D. E., Predatory Bacteria Attenuate Klebsiella pneumoniae Burden in Rat Lungs. mBio 2016, 7 (6), e01847-16.

Shanks, R. M.; Davra, V. R.; Romanowski, E. G.; Brothers, K. M.; Stella, N. A.; Godboley, D.; Kadouri, D. E., An Eye to a Kill: Using Predatory Bacteria to Control Gram-Negative Pathogens Associated with Ocular Infections. PLoS One 2013, 8 (6), e66723.

Romanowski, E. G.; Stella, N. A.; Brothers, K. M.; Yates, K. A.; Funderburgh, M. L.; Funderburgh, J. L.; Gupta, S.; Dharani, S.; Kadouri, D. E.; Shanks, R. M. Q., Predatory bacteria are nontoxic to the rabbit ocular surface. Sci Rep—Uk 2016, 6, 30987-30987.

Madhusoodanan, J., Inner Workings: Probing predatory bacteria as an antibacterial remedy. Proc. Natl. Acad. Sci. 2019, 116 (46), 22887-22890.

Jiang, J.; Moore, J. S.; Edelhauser, H. F.; Prausnitz, M. R., Intrascleral Drug Delivery to the Eye Using Hollow Microneedles. Pharm. Res. 2009, 26 (2), 395-403.

Than, A.; Liu, C.; Chang, H.; Duong, P. K.; Cheung, C. M. G.; Xu, C.; Wang, X.; Chen, P., Self-implantable double-layered micro-drug-reservoirs for efficient and controlled ocular drug delivery. Nat. Commun. 2018, 9 (1), 4433.

Bharathi, M. J.; Ramakrishnan, R.; Maneksha, V.; Shivakumar, C.; Nithya, V.; Mittal, S., Comparative bacteriology of acute and chronic dacryocystitis. Eye 2008, 22 (7), 953-960.

Fleiszig, S. M. J.; Evans, D. J., Pathogenesis of contact lens-associated microbial keratitis. Optom Vis Sci 2010, 87 (4), 225-232.

Teweldemedhin, M.; Gebreyesus, H.; Atsbaha, A. H.; Asgedom, S. W.; Saravanan, M., Bacterial profile of ocular infections: a systematic review. BMC Ophthalmol 2017, 17 (1), 212-212.

Chung, C. Y.; Wong, E. S.; Liu, C. C. H.; Wong, M. O. M.; Li, K. K. W., Clinical features and prognostic factors of Klebsiella endophthalmitis—10-year experience in an endemic region. Eye 2017, 31 (11), 1569-1575.

Shatzkes, K.; Chae, R.; Tang, C.; Ramirez, G. C.; Mukherjee, S.; Tsenova, L.; Connell, N. D.; Kadouri, D. E., Examining the safety of respiratory and intravenous inoculation of Bdellovibrio bacteriovorus and Micavibrio aeruginosavorus in a mouse model. Sci Rep—Uk 2015, 5 (1), 12899.

Dashiff, A.; Junka, R. A.; Libera, M.; Kadouri, D. E., Predation of human pathogens by the predatory bacteria Micavibrio aeruginosavorus and Bdellovibrio bacteriovorus. J. Appl. Microbiol. 2011, 110 (2), 431-444.

Heichel, J.; Wilhelm, F.; Kunert, K. S.; Hammer, T., Topographic Findings of the Porcine Cornea. Med Hypothesis Discov Innov Ophthalmol 2016, 5 (4), 125-131.

Selk Ghaffari, M.; Sabzevari, A.; Khorami, N.; Vahedi, H., Successful treatment of severe conjunctivitis and blepharitis caused by *Escherichia coli* in an ostrich (*Struthio camelus*). Comp Clin Path 2010, 19 (1), 121-123.

Anagaw, B.; Biadglegne, F.; Belyhun, Y.; Anagaw, B.; Mulu, A., Bacteriology of ocular infections and antibiotic susceptibility pattern in Gondar University Hospital, north west Ethiopia. Ethiop Med J 2011, 49 (2), 117-123.

Lorenzo, D., Chloramphenicol Resurrected: A Journey from Antibiotic Resistance in Eye Infections to Biofilm and Ocular Microbiota. Microorganisms 2019, 7 (9).

Daroy, M. L. G.; Lopez, J. S.; Torres, B. C. L.; Loy, M. J.; Tuano, P. M. C.; Matias, R. R., Identification of unknown ocular pathogens in clinically suspected eye infections using ribosomal RNA gene sequence analysis. Clin. Microbiol. Infect. 2011, 17 (5), 776-779.

Iebba, V.; Totino, V.; Santangelo, F.; Gagliardi, A.; Ciotoli, L.; Virga, A.; Ambrosi, C.; Pompili, M.; De Biase, R. V.; Selan, L.; Artini, M.; Pantanella, F.; Mura, F.; Passariello, C.; Nicoletti, M.; Nencioni, L.; Trancassini, M.; Quattrucci, S.; Schippa, S., Bdellovibrio bacteriovorus directly attacks Pseudomonas aeruginosa and *Staphylococcus aureus* Cystic fibrosis isolates. Front Microbiol 2014, 5, 280.

Dharani, S.; Kim, D. H.; Shanks, R. M. Q.; Doi, Y.; Kadouri, D. E., Susceptibility of colistin-resistant pathogens to predatory bacteria. Res. Microbiol. 2018, 169 (1), 52-55.

Meek, R. W.; Cadby, I. T.; Moynihan, P. J.; Lovering, A. L., Structural basis for activation of a diguanylate cyclase required for bacterial predation in Bdellovibrio. Nat. Commun. 2019, 10 (1), 4086.

Tang, B.-L.; Yang, J.; Chen, X.-L.; Wang, P.; Zhao, H.-L.; Su, H.-N.; Li, C.-Y.; Yu, Y.; Zhong, S.; Wang, L.; Lidbury, I.; Ding, H.; Wang, M.; McMinn, A.; Zhang, X.-Y.; Chen, Y.; Zhang, Y.-Z., A predator-prey interaction between a marine *Pseudoalteromonas* sp. and Gram-positive bacteria. Nat. Commun. 2020, 11 (1), 285.

Yu, R.; Zhang, S.; Chen, Z.; Li, C., Isolation and application of predatory Bdellovibrio- and-like organisms for municipal waste sludge biolysis and dewaterability enhancement. Front Environ Sci Eng 2017, 11 (1), 10.

Atterbury, R. J.; Hobley, L.; Till, R.; Lambert, C.; Capeness, M. J.; Lerner, T. R.; Fenton, A. K.; Barrow, P.; Sockett, R. E., Effects of Orally Administered Bdellovibrio bacteriovorus on the Well-Being and *Salmonella* Colonization of Young Chicks. Appl. Environ. Microbiol. 2011, 77 (16), 5794-5803.

Chen, H.-J.; Lin, D.-a.; Liu, F.; Zhou, L.; Liu, D.; Lin, Z.; Yang, C.; Jin, Q.; Hang, T.; He, G.; Xie, X., Transdermal Delivery of Living and Biofunctional Probiotics through Dissolvable Microneedle Patches. ACS Appl. Bio Mater. 2018, 1 (2), 374-381.

Cao, H.; Wang, H.; Yu, J.; An, J.; Chen, J., Encapsulated Bdellovibrio Powder as a Potential Bio-Disinfectant against Whiteleg Shrimp-Pathogenic Vibrios. Microorganisms 2019, 7 (8), 244.

Leone, M.; van Oorschot, B. H.; Nejadnik, M. R.; Bocchino, A.; Rosato, M.; Kersten, G.; O'Mahony, C.; Bouwstra, J.; van der Maaden, K., Universal Applicator for Digitally-Controlled Pressing Force and Impact Velocity Insertion of Microneedles into Skin. Pharmaceutics 2018, 10 (4), 211.

\* cited by examiner

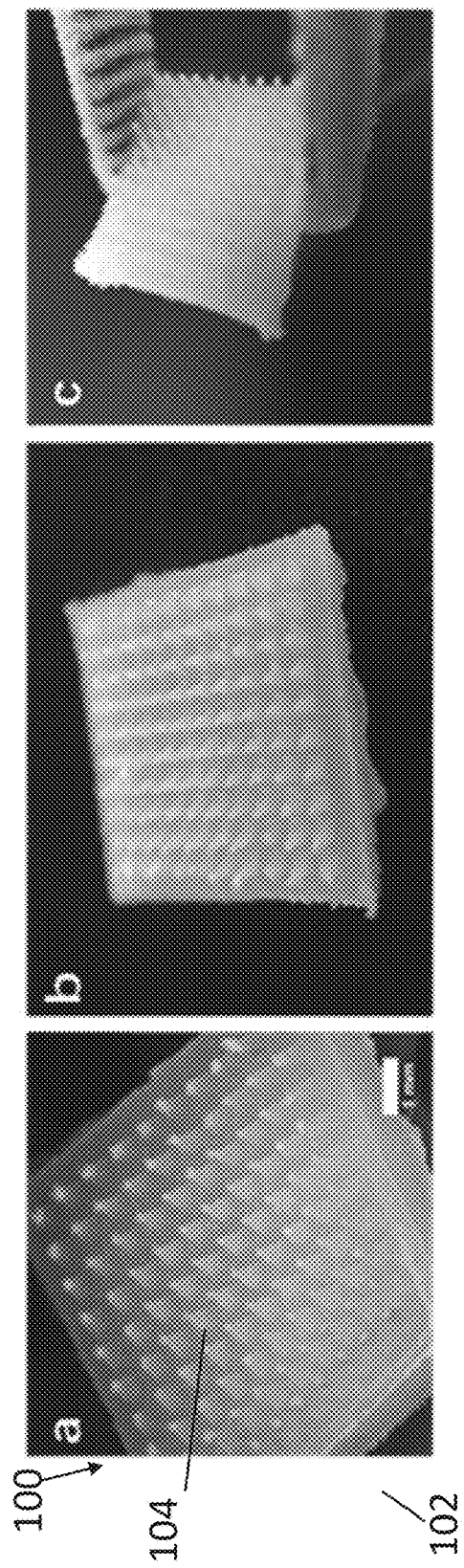
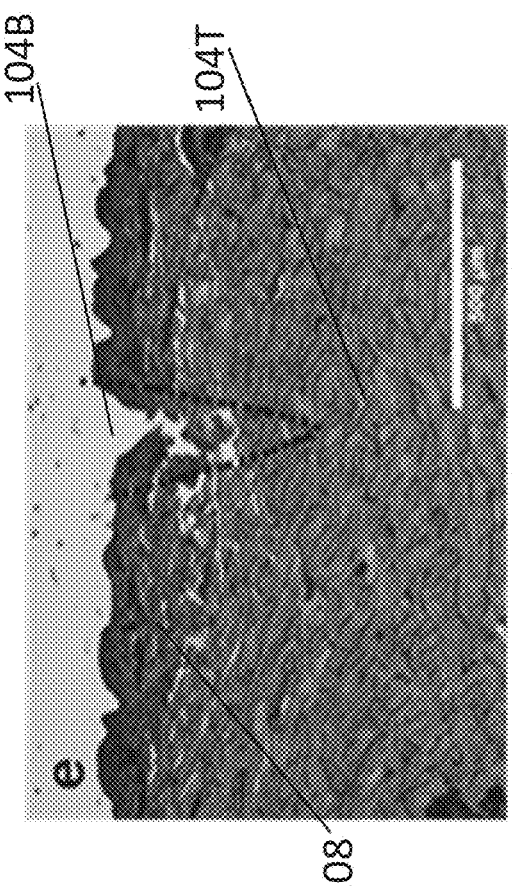
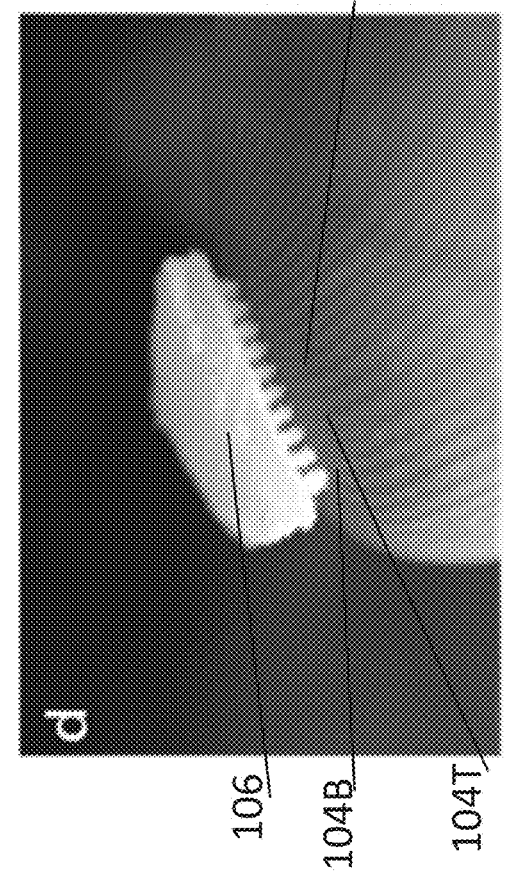
FIG. 1A  FIG. 1B  FIG. 1C  FIG. 1D  FIG. 1E

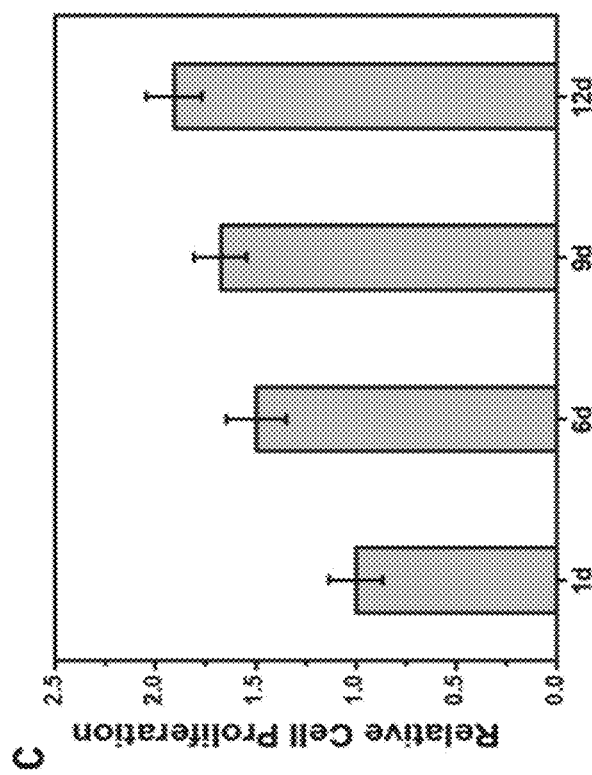
FIG. 6A
FIG. 6B
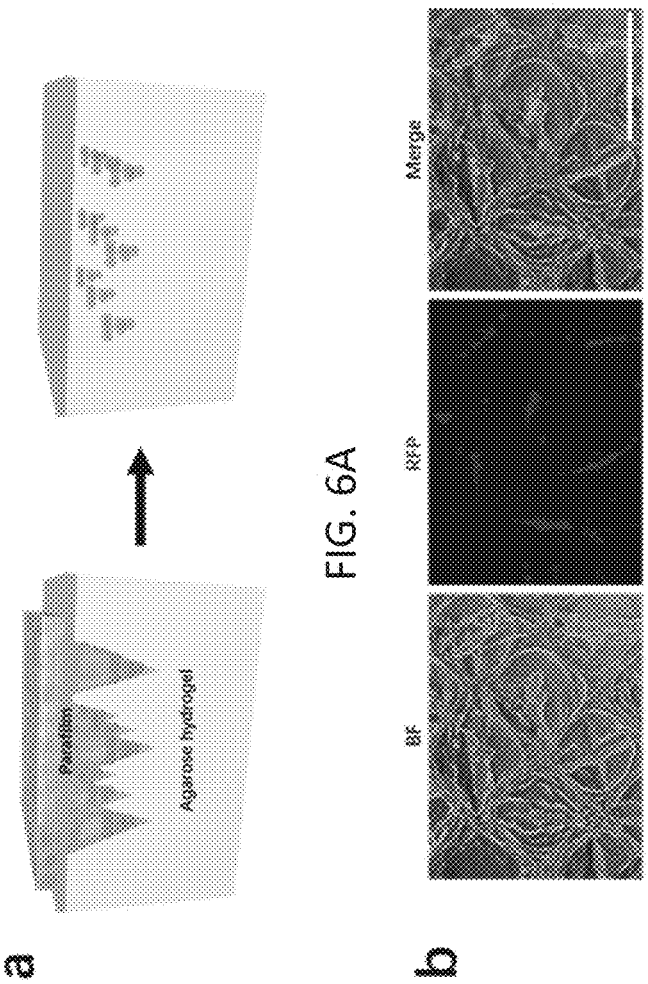
FIG. 6C

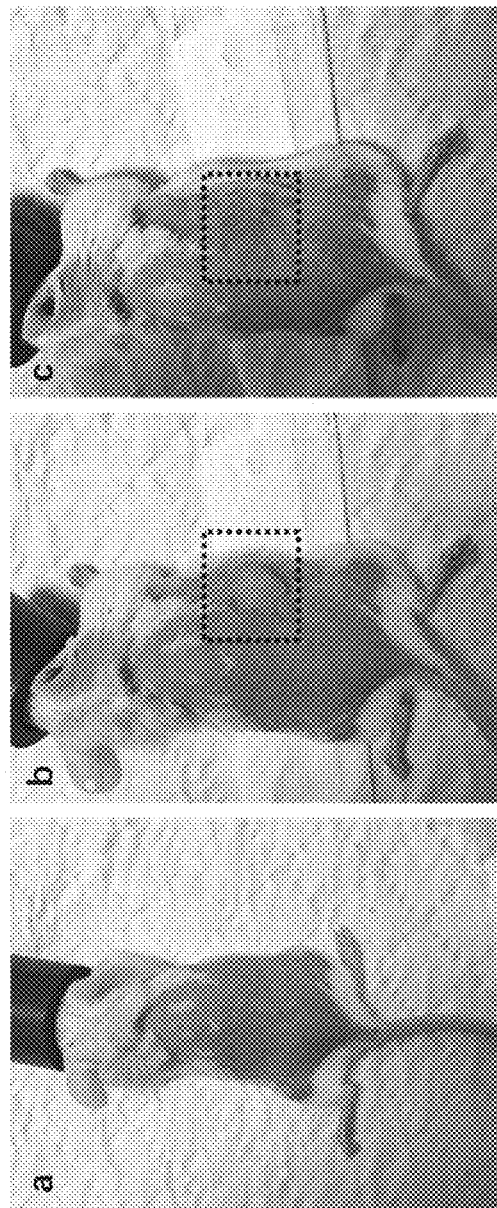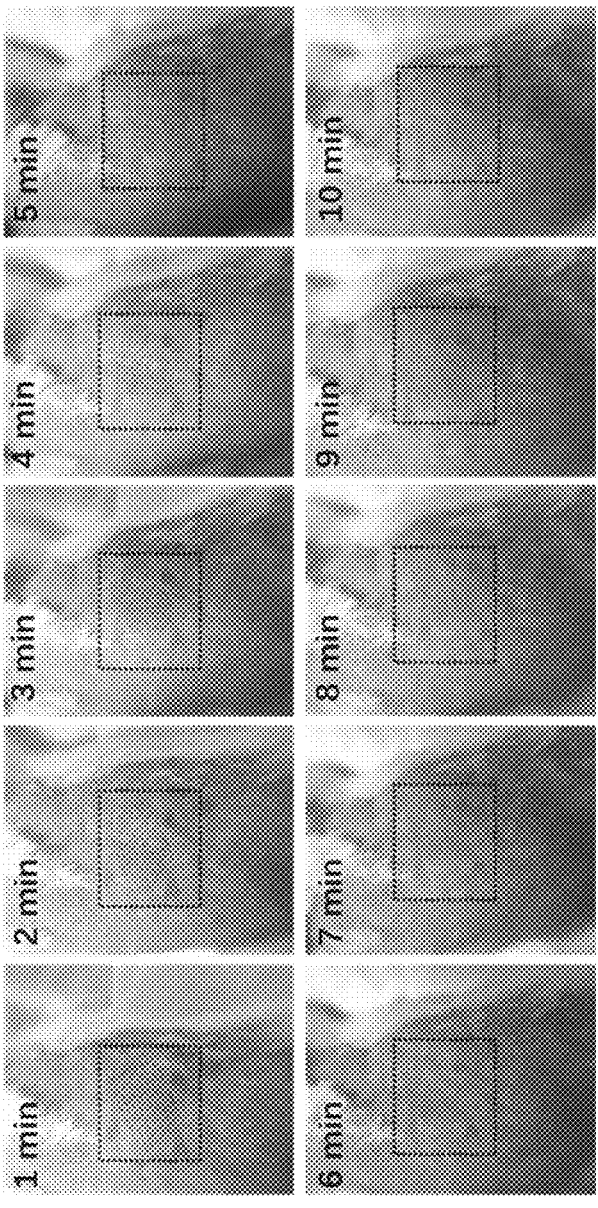
FIG. 8A  FIG. 8B  FIG. 8C  FIG. 8D

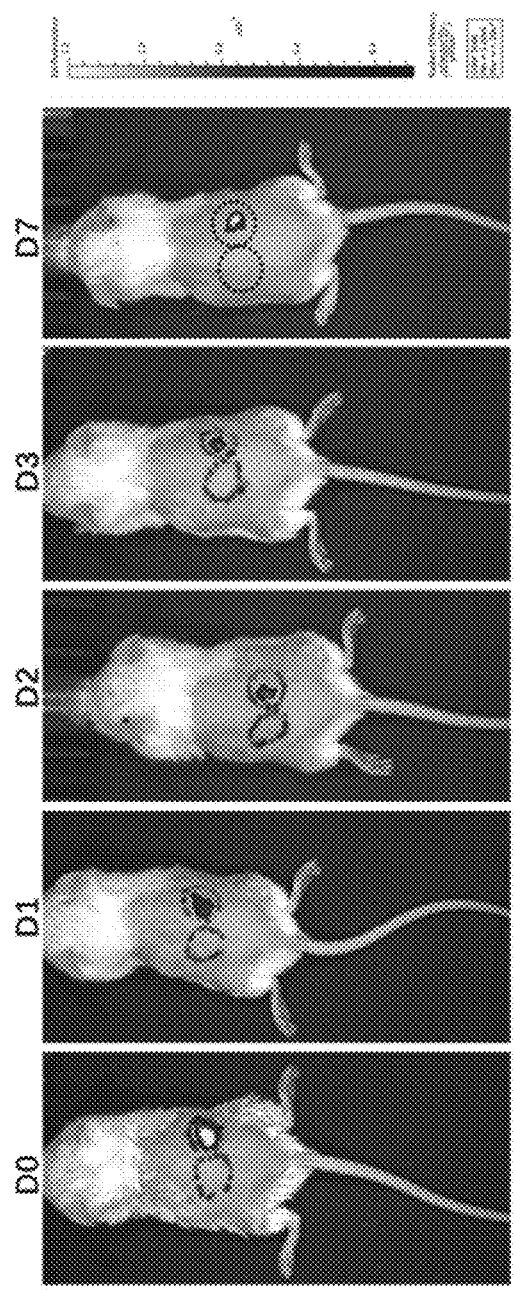
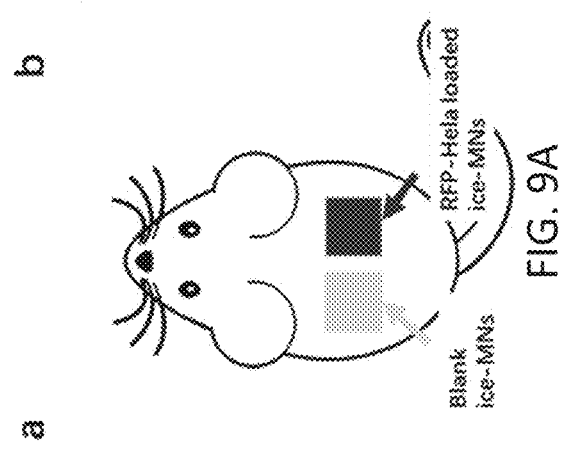
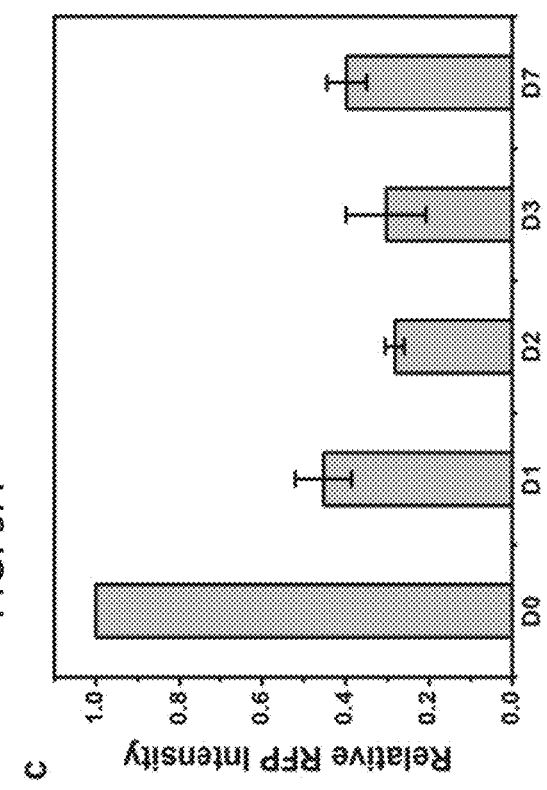
FIG. 9A
FIG. 9B
FIG. 9C

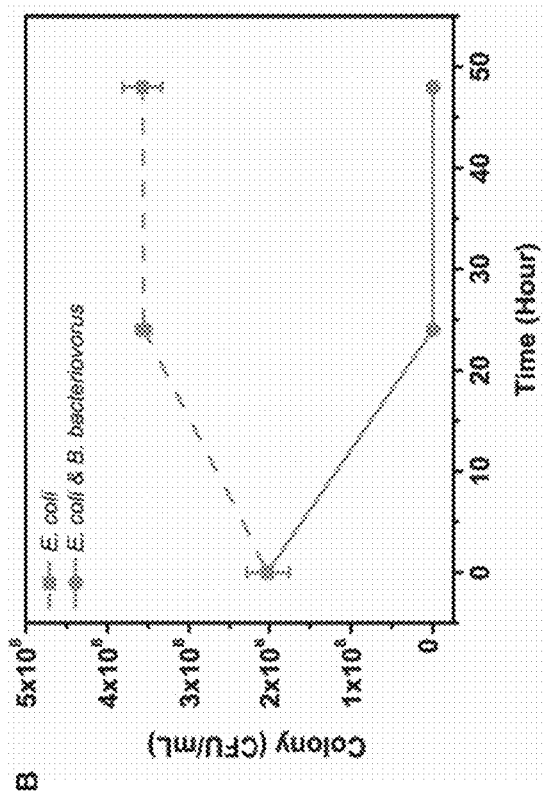
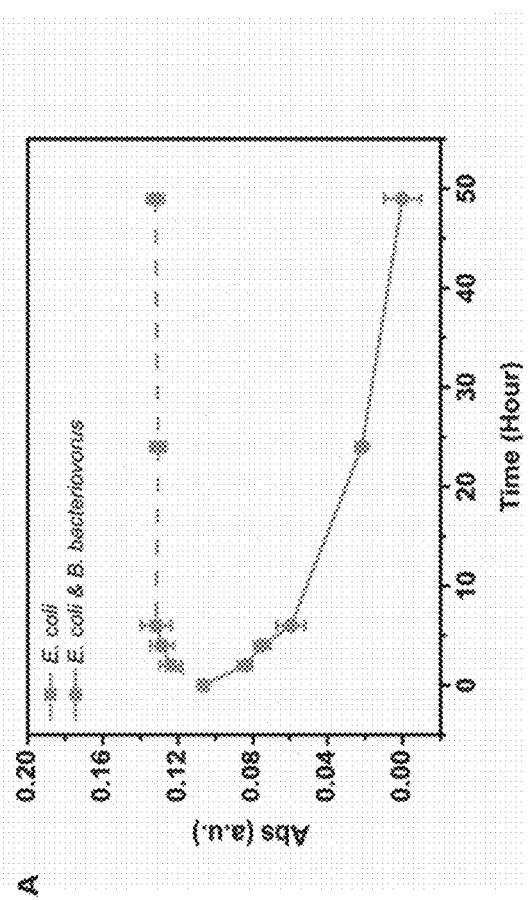
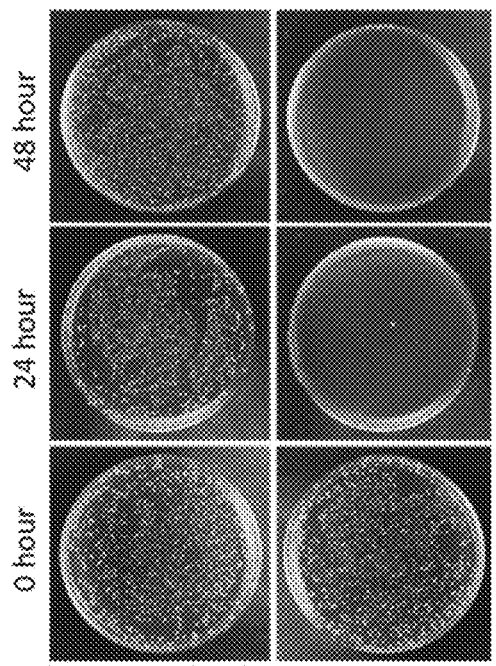
FIG. 20A
FIG. 20B
FIG. 20C

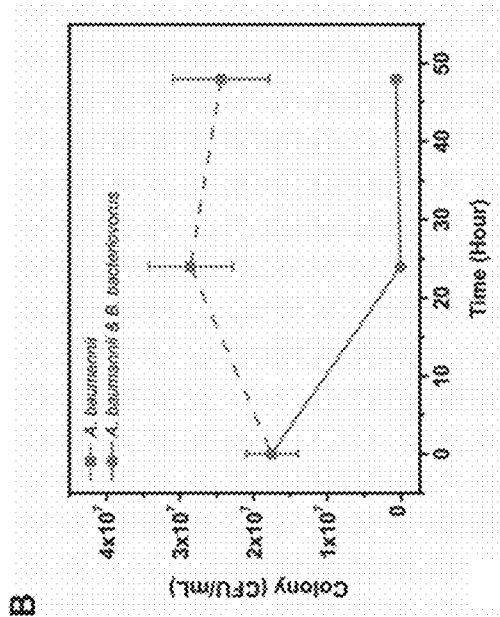
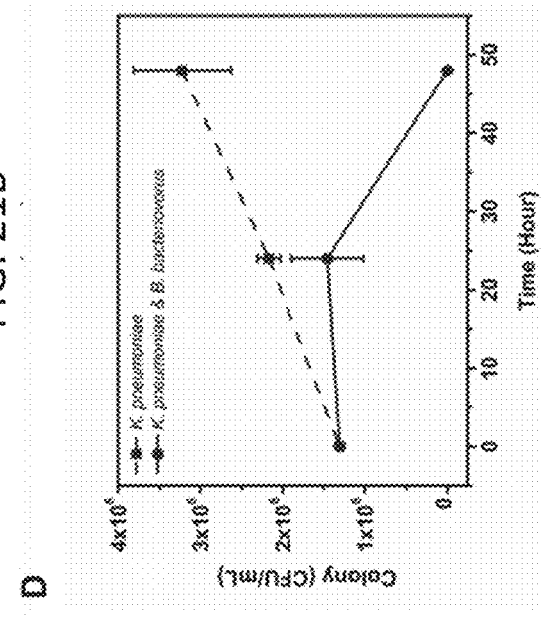
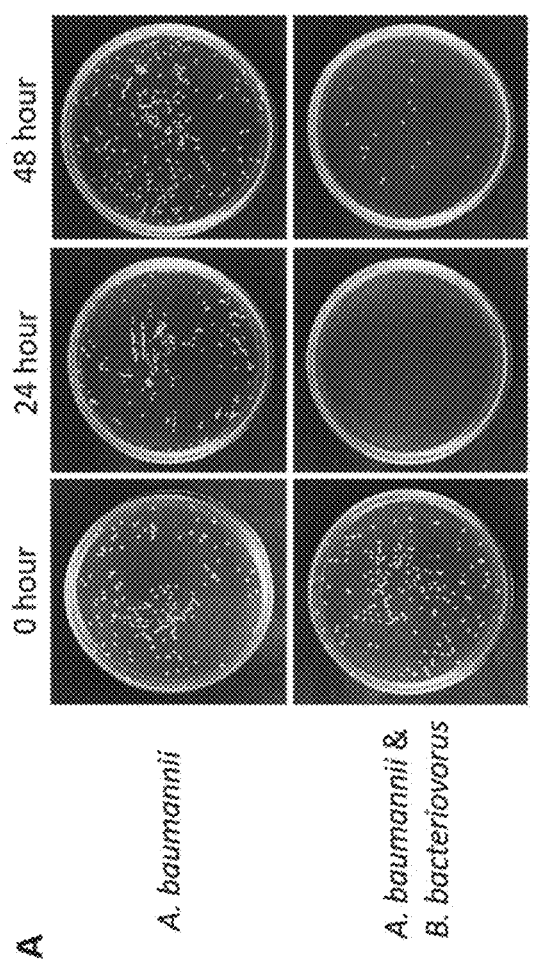
FIG. 21A
FIG. 21B
FIG. 21C
FIG. 21D

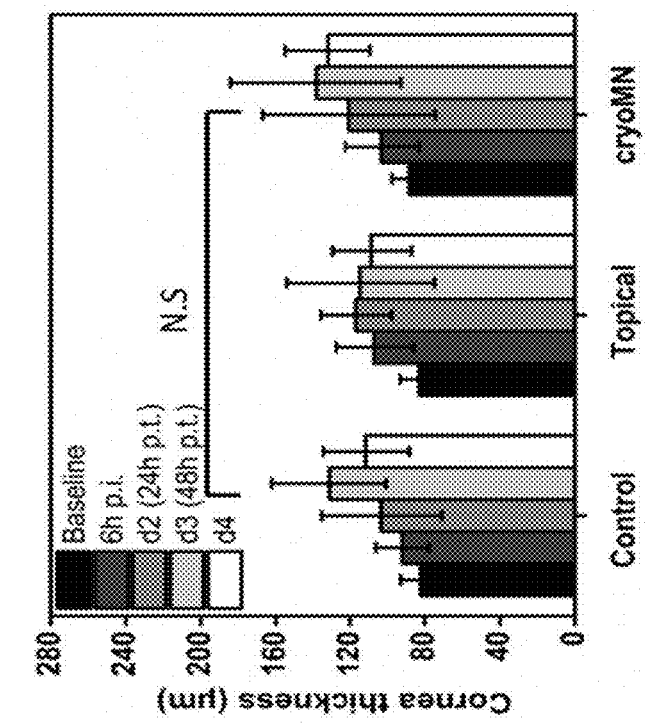
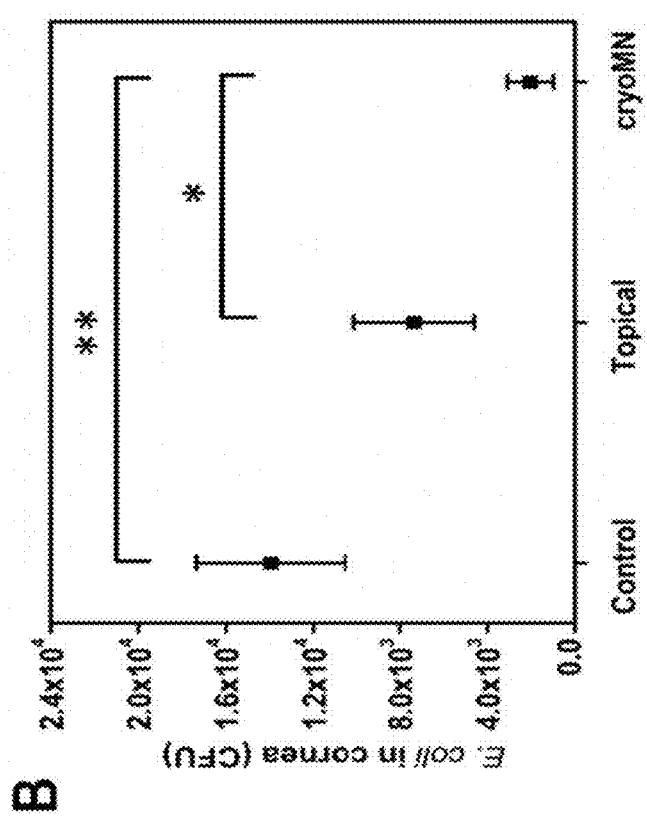
FIG. 23C
FIG. 23B

CRYO FORMULATION-BASED MICRONEEDLE DEVICE FOR OCULAR DELIVERY OF BIOACTIVE THERAPEUTIC AGENTS USING A CRYO-MICRONEEDLE PATCH

TECHNICAL FIELD

The present invention relates to a cryo formulation-based microneedle device for ocular delivery of bioactive therapeutic agents, in particular, but not limited to ocular delivery of predatory bacteria with cryomicroneedles against eye infection.

BACKGROUND

Delivery of bioactive agents is of great potential for treatment skin diseases. For example, melanocyte suspensions have been used clinically to vitiligo. Intradermal injection of fibroblast or mesenchymal stem cell was used for wound healing in recessive dystrophic epidermolysis bullosa.

In addition to treat skin diseases, transplantation of cells is also used in the field of facelift and hair regeneration. For example, injection of fibroblast can help restore the elasticity of skin and reduce winkles because fibroblasts can produce a large amount of collagen which can recover skin.

SUMMARY OF THE INVENTION

In accordance with a first aspect the present invention, there is provided a cryo formulation-based microneedle device for transdermal delivery of bioactive therapeutic agents, comprising: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on cornea of an eye, in which the miniaturized needles penetrates into the eye; and wherein the miniaturized needles is further arranged to melt so as to release one or more bioactive therapeutic agents into the eye to achieve a targeted therapeutic effect.

In an embodiment the first aspect, each of the one or more microneedle patches consisting of a matrix solution and the bioactive therapeutic agents.

In an embodiment the first aspect, the bioactive therapeutic agents comprise a plurality of biological cells including at least one of cancer cells, fibroblasts, endothelial cells, smooth muscle cells, stem cells, melanocytes, dendritic cells, neutrophils, and T-cells.

In an embodiment the first aspect, the bioactive therapeutic agents comprise a biochemical substance including at least one of drugs, vaccines, proteins, peptides, nucleic acids, virus and fungi.

In an embodiment the first aspect, the bioactive therapeutic agents comprise bacteria.

In an embodiment the first aspect, the bioactive therapeutic agents comprise predatory bacteria.

In an embodiment the first aspect, the bioactive therapeutic agents comprise *Bdellovibrio Bacteriovorus* (*B. bacteriovorus*).

In an embodiment the first aspect, the therapeutic effect includes eye infection treatment.

In an embodiment the first aspect, the matrix solution consists of an aqueous base solution and a cryoprotectant.

In an embodiment the first aspect, the aqueous base solution comprises at least one of water, phosphate-buffered saline (PBS), glycerol and 4-(2-hydroxyethyl)-1-piperazineethanesulfonic acid (HEPES).

In an embodiment the first aspect, the cryoprotectant include at least one of dimethyl sulfoxide (DMSO), glycerol, ethylene glycol, sucrose, fructose, trehalose, galactose, dextrose and proteins.

In an embodiment the first aspect, the cryoprotectant include at least one of poly(ethylene glycol) (PEG), polyvinylpyrrolidone (PVP), polyvinyl alcohol (PVA), poly-l-lysine, hyaluronic acid (HA), starch, gelatin, agarose, alginate, chitosan, cellulose, carboxymethyl cellulose (CMC), collagen, chitin, dextran, guar gum, pullulan, xanthan, xyloglucan, heparin, chondroitin, keratan, mucin, and their derivatives thereof.

In accordance with a second aspect the present invention, there is provided a method of fabricating a microneedle device in the first aspect, comprising the steps of: casting the matrix solution containing the bioactive therapeutic agents into a mold defined with an array of microneedle structures; freezing the solution to define the array of microneedle structures on the microneedle patches; and dethatching the microneedle patches from the mold.

In an embodiment the second aspect, the mold includes a PDMS mold and/or a metal mold.

In an embodiment the second aspect, the method further comprises the step of urging the bioactive therapeutic agents and/or the matrix solution into the array of microneedle structures define on the mold.

In an embodiment the second aspect, the bioactive therapeutic agents and/or the matrix solution are driven into the mold using centrifugation or sedimentation.

In an embodiment the second aspect, the method further comprises step of fabricating the PDMS mold using the metal mold, wherein the PDMS mold is a negative mold and the metal mold is a positive template defined with a predetermined pattern of the array of microneedle structures.

In an embodiment the second aspect, the method further comprises the step of storing the microneedle patches at below −80'C.

In an embodiment the third aspect, there is provided a method of using the microneedle device of the first aspect, comprising the step of: removing the microneedle device from a storage place; and applying the microneedle device within a predetermined period of time after removal from the storage place.

In an embodiment the third aspect, the predetermined period of time is 30 seconds.

In an embodiment the third aspect, the microneedle patches are arranged to facilities a predetermined penetration depth of the bioactive therapeutic agents into the eye.

In an embodiment the third aspect, the predetermined penetration depth is 50-1000 μm.

In an embodiment the third aspect, the method further comprises the step of temporally attaching the microneedle device to a handle, thereby allowing an operator to apply the microneedle device by holding the handle.

The term "comprising" (and its grammatical variations) as used herein are used in the inclusive sense of "having" or "including" and not in the sense of "consisting only of".

It should be understood that alternative embodiments or configurations may comprise any or all combinations of two or more of the parts, elements or features illustrated, described or referred to in this specification.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, in any other country.

As used herein, the term "and/or" includes any and all possible combinations or one or more of the associated listed items, as well as the lack of combinations when interpreted in the alternative ("or").

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Details and embodiments of the indoor navigation method and system will now be described, by way of example, with reference to the accompanying drawings in which:

FIGS. 1A to 1D are images showing different view of the ice microneedles integrated with living cells in accordance with embodiments of the present invention;

FIG. 1E is an image showing an H&E-stained cross-section of porcine skin after being penetrated by ice microneedles of FIG. 1A;

FIGS. 4A and 4B illustrate the viability of different types of cells after recovering from ice-MNs (freezer at −80° C.) patches and ice-MNs (LN) after 1 day storage, in which FIG. 4A shows live (green)/dead (red) staining of loaded cells, with the scale bar of 200 μm, and FIG. 46 is a plot showing quantitative data of viability obtained from the Live/Dead staining and Alarmablue™ viability assay;

FIGS. 6A to 6D illustrates a delivery of RFP-Hela cells into 3D hydrogel system, the RFP-Hela loaded ice-MNs were storage in LN for 1 day, and in which: FIG. 6A is a schematic illustration of ice-MNs(LN) penetrating into fake skin model made from 1.4% agarose gel and parafilm; FIG. 6B are microscopic images showing a top view of the hydrogel after application of ice-MN patches; FIG. 6C is a plot showing the proliferation of RFP-Hela cells after being delivered into hydrogel; and FIG. 6D is a z-stack showing the 3D hydrogel system in 1, 6, 9 and 12 days respectively;

FIGS. 8A to 8D are images showing an application of ice-MNs on mice, the RFP-Hela loaded ice-MNs were storage in LN for 1 day, in which FIGS. 7A to 7C respectively shows before (a), during (b) and after (c) application of ice-MNs (LN) on mice skin, wherein FIG. 7D shows a series of images showing the skin recovery post the treatment, and the microholes made by MN patch gradually disappeared within 10 min;

FIG. 9A is a Schematic diagram showing an application of RFP-Hela loaded ice-MNs (LN) in the mice model;

FIG. 9B are in vivo fluorescence images of RFP secreted by RFP-Hela after being delivered into skin;

FIG. 9C is a plot showing the quantitative data of RFP intensity in mice skin along with the time;

FIG. 13A to 13D shows the morphology and melting behaviour of cryoMNs, in which FIG. 13A is a photographic image of intact cryoMNs (scale bar: 1 mm); FIG. 13B is a plot showing quantification of MN tip lengths after exposure to RT and body temperature; FIGS. 13C and 13 D are images showing cryoMN melting behavior, respectively, in the air and on human finger tips, scale bar is 2 mm in both FIGS. 13C and 13D;

FIGS. 15A and 15B illustrates optimization of cryoMN formulation, in which FIG. 14A is a plot showing the viabilities of B. bacteriovorus cryopreserved in cryoMN formulations with different glycerol concentrations through the 14-day storage, N=5; and FIG. 14B is a plot showing the loading force-displacement profiles of cryoMNs with different glycerol concentrations, N=4.  p<0.01, * p<0.001, N.S means no significant difference;

FIGS. 17A to 17C illustrates the penetration capability of cryoMNs into agarose gel and porcine cornea, in which FIG. 17A is a confocal image showing the penetration of cryo-MNs and the delivery of bacteria in agarose gel; FIG. 17B are images of porcine cornea with pots created by cryoMNs, the scale bar is 400 μm; and FIG. 17C are H&E-stained cross-section images of porcine cornea after treatment with cryoMNs taken out from the freezer and left in the air for different times, the scale bar is 100 μm;

FIGS. 19A to 19C illustrates the in vitro predation efficiency of predatory bacteria, in which FIG. 19A is an image showing that *B. bacteriovorus* can "eat" *E. coli* and form clear spots on plates, FIG. 19B is a plot showing time-dependent optical density changes after incubation with prey cells measured by BioTek plate reader, and FIG. 19C is a plot showing time-dependent changes of bacterial concentrations after incubation with prey cells measured by CFU plating;

FIGS. 20A to 20C shows in vitro predation efficiency of *B. bacteriovorus* predatory bacteria delivered using cryo-MNs against *E. coli* (ATCC25922), in which FIGS. 20A and 20B are plots showing time-dependent changes of *E. coli* concentrations with or without cryoMN treatment measured respectively (A) by optical density at 600 nm and (B) by CFU plating; and FIG. 20C is are optical images of CFU plating (dilution factor of $10^{-4}$);

FIGS. 21A to 21D illustrates in vitro predation effects of *B. bacteriovorus* predatory bacteria delivered using cryo-MNs against *A. baumannii* and *K. pneumoniae*; in which FIG. 21A are optical images of agar plates and FIG. 21B is a plot showing the change of *A. baumannii* concentration without or with *B. bacteriovorus* cryoMNs (dilution factor of 104); FIG. 21C are optical images of agar plates and FIG. 21D is a plot an showing the change of *K. pneumoniae* concentration without or with *B. bacteriovorus* cryoMNs (dilution factor of $10^{-5}$);

FIGS. 23A to 23C illustrates ocular delivery of *B. bacteriovorus* with cryoMNs for eye infection, in which FIG. 23A are cornea images taken by slit-lamp photography (a. Baseline; b. 6 h p.i. after inoculation (prior treatment); c. Day 2 (24 h p.i.); d. Day 3; e. Day 4; FIG. 23B is a plot showing final *E. coli* concentration inside mouse corneas, where N=4; and FIG. 23C is a plot showing cornea thickness before and after treatment every day, where N=4, and * p<0.1, ** p<0.01, N.S means no significant difference.

DETAILED DESCRIPTION OF THE PREFERRED EMBODIMENT

Figure 2:
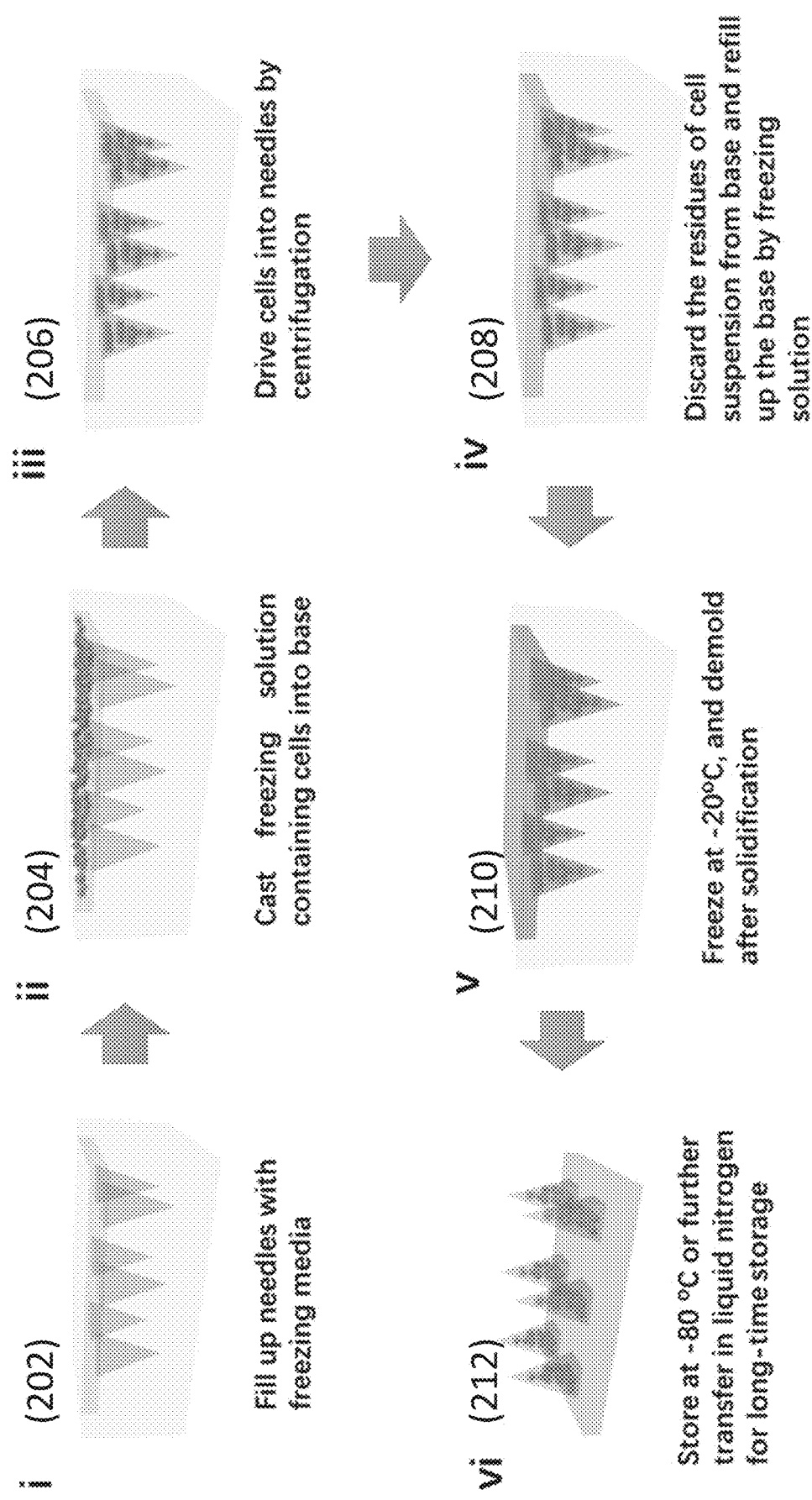
FIG. 2 is an illustration showing a process flow of a fabrication of ice microneedles integrated with living cells in accordance with an embodiment of the present invention.

The inventors, through their own research, trials and experiments, devised that microneedles (MNs) are an array of miniaturized needles down to the micrometer scale and they are initially developed for transdermal delivery of drugs and vaccines. They allow for the minimally-invasive perturbation of the stratum corneum barrier and controlled and targeted delivery of therapeutic agents in pain-free and blood-free fashion. Recently, they are also used for the extraction of blood and interstitial fluid for biomarker analysis. MN-based devices have low risk of infection, needle-phobic and needle-stick injury and cross-contamination.

In some example embodiments, MNs may be made of silicon, metals (e.g. stainless-steel and titanium), ceramics, and polymers. However, silicon, metal and ceramics based MNs suffer from the limited drug loading, potential break-up in skin, or complicated and expensive fabrication procedures, and polymer MNs are limited by the low drug loading and inability to maintain the activity and deliver fragile active agents such as protein, plasmid, stem cells, immune cells, bacteria, and virus.

In accordance with an embodiment of the present invention, there is provided a new class of MN device, the cryo formulation-based MN device (cryo MNs, or ice MNs), which is significantly different from the abovementioned MN platforms in terms of materials, formulations, and fabrication protocols.

Preferably, this device is made of aqueous solutions and bioactive therapeutic agents (eg. cells, drugs, and proteins, et al.) and fabricated by freezing to form the cryo status. The formulation is optimized to maximize the bioactivity of therapeutic agents while providing sufficient mechanical properties for the ice MNs to penetrate into the skin layers. Finally, the ice MNs are usually made right before usage within the template (can be less than 4 hours), but can be stored for at least 1 month without loss of bioactivity or viability.

In one example embodiment, the invention provides a direct integration of cells and delivery of cells with ice MNs. The inventors devise that all other MN platforms except hollow MNs are not suitable for cell delivery, and although hollow MNs may be used to deliver cells through pressure-based injection, such system lacks of control of the injection depth, cell number, and pattern of cells.

Preferably, the ice MNs is the first type of solid MN that can deliver cells and directly integrate cells into MNs. It offers a convenient strategy to control the location, density and types of delivered cells in skin.

With reference to FIGS. 1A to 1E, there is shown an example embodiment of a cryo formulation-based microneedle device 100 for transdermal delivery of bioactive therapeutic agents, comprising: one or more microneedle patches 102 each including an array of miniaturized needles 104, wherein each miniaturized needle 104 defining a base end and a tip 104T; and a substrate 106 to which the base end of the array of miniaturized needles 104 is attached or integrated thereto; wherein the microneedle patch 102 is in a cryo status; wherein each of the one or more microneedle patch 102 is adapted to be applied on a skin surface 108, in which the miniaturized needles 104 penetrates into skin; and wherein the miniaturized needles 104 is further arranged to melt so as to release one or more bioactive therapeutic agents into the skin to achieve a targeted therapeutic effect.

In this example, the microneedle patches 102 consisting of a matrix solution containing a bioactive therapeutic agents being freezed in the solid state, such that when the ice microneedle patches 102 is subjected to heat at the skin surface 108 and/or from the environment, it melts gradually and hence the bioactive therapeutic agents is released into the skin as the patch 102 melts.

Examples of bioactive therapeutic agents may includes biological cells, such as but not limited to cancer cells, fibroblasts, endothelial cells, smooth muscle cells, stem cells, melanocytes, dendritic cells, neutrophils, and T-cells. Alternatively or additionally, the bioactive therapeutic agents may include other biochemical substances such as but not limited to drugs, vaccines, proteins, peptides, nucleic acids, bacteria, virus and fungi.

The bioactive therapeutic agents may be contained in a matrix solution, comprising an aqueous base solution and a cryoprotectant, such that the matrix solution and the bioactive therapeutic agents may be molded to have the shape of the microneedles 104 with the base. Examples of the aqueous base solution includes one or more of water, phosphate-buffered saline (PBS), glycerol and 4-(2-hydroxyethyl)-1-piperazineethanesulfonic acid (HEPES), and these aqueous base solution may be solidified upon freezing.

For example, the ice-MNs that were finally frozen either in −80° C. or liquid nitrogen (LN) were named as ice-MNs (−80° C.) and ice-MNs (LN), respectively. The morphology of ice MNs 104 is shown in the FIGS. 1A to 1D. In this example, the obtained ice-MNs 104 displayed a height of ~900 μm with a base width of about 350 μm and inter-needle spacing of about 350 μm. According to the dimension of ice-MN patch 102 and volume formula of rectangular pyramid, the volume of solution in each needle cavity was about $3.7 \times 10^{-2}$ μL. In addition, referring to FIG. 1E, the ice MNs can easily penetrate cross the epidermis and reach to dermis. It should be appreciated by a skilled person in the art that the dimension or design parameters of the MNs including the size, pitch, height and shape of the needles, as well as the area of the MNs array may be changed according to different application which requires delivery of bioactive therapeutic agents through the skin surface.

The formulation of solution for preparing ice MN depends on the desired active agents that will be delivered. The following table lists a number of example choice of several freezing solutions for different active agents.

| Active agents | Solutions |
| --- | --- |
| Cells | Water + cryoprotectants (such as 2.5% DMSO, 100 mM sucrose) |
| Protein/peptides | Water/PBS + 1 mg/mL Bovine serum albumin (BSA) |
| DNA/RNA | Water/PBS + 1 mg/mL polycation (such as poly-l-lysine, chitosan, collagen) |
| Small molecular drugs | Water/PBS |

With reference to FIG. 2, there is shown an example fabrication process 200 for fabricating the microneedle device 100 in accordance with embodiments of the present invention. The method 200 of fabrication comprises the steps of: casting the matrix solution containing the bioactive therapeutic agents into a mold, such as a PDMS mold, defined with an array of microneedle structures; freezing the solution to define the array of microneedle structures on the microneedle patches; and dethatching the microneedle patches from the mold. Alternatively, a metal mold, such as a stainless steel mold, may be used.

Optionally, the method further comprises the step of urging the bioactive therapeutic agents and/or the matrix solution into the array of microneedle structures define on the mold, such as by using centrifugation, or simply by natural sedimentation.

Take 2.5% wt DMSO combined with 100 mN sucrose as an example, to fabricate ice MNs 104 for cell delivery, at step 202, the mold defining the shape of the needles may be filled up with the freezing media, such as the matrix solution or the mixture of 2.5% wt DMSO combined with 100 mM sucrose. At step 204, cells contained in a freezing solution such as water and/or the cryoprotectants are casted to the mold at the base. At step 206, the cells are driven into the needle structures using centrifugation. At step 208, the residues of cell suspension from the base may be discarded, and then the base of the mold may be refilled to form the base of the MN device. At step 210, the matrix solution and the cells are frozen below the melting point of the matrix solution, e.g. at −20° C., followed by demolding the frozen patch after solidification. Finally, at step 212, the fabricated cryo formulation-based microneedle device may be stored under −80° C. and/or any other suitable environment, such as in liquid nitrogen, for long-time storage if necessary.

In an alternative example, to fabricate ice MNs for small molecular drug delivery, small molecular drug may be dissolved in aqueous with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

Alternatively, to fabricate ice MNs for proteins/peptides delivery, proteins/peptides and BSA (1 mg/mL) may be dissolved in aqueous solution with desired concentrations. The prepared solution is casted into PDMS mold and followed by centrifugation. Then the PDMS mold is put at −20° C. for 2 hours and then transferred to −80° C. Then Ice MNs integrated with small molecular drugs can be peeled out of PDMS mold before applications.

Yet alternatively, to fabricate ice MNs for DNA/RNA delivery, the DNA/RNA and polycations (1 mg/mL) are dissolved in aqueous solution with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

The solutions for making ice MNs consist of aqueous base solutions and cryoprotectants. The aqueous base solutions may include water, PBS, and/or HEPES. The cryoprotectants include DMSO, glycerol, ethylene glycol, sucrose, fructose, trehalose, galactose, dextrose, proteins, or any types of combination of two or more cryoprotectants. The cryoprotectants also include polyvinylpyrrolidone, polyvinyl alcohol, poly-l-lysine, HA, starch, gelatin, agarose, alginate, chitosan, cellulose, collagen, chitin, dextran, guar gum, pullulan, xanthan, xyloglucan, and their derivatives, and the combinations thereof. In addition, the cryoprotectants include the hydrogel systems made from abovementioned polymers.

To optimize the freezing solution for cell delivery, in an experiment performed by the inventors, six types of cells, including Hela-red fluorescent protein (RFP) stable human cell line (RFP-Hela), human keratinocytes (HACAT), human normal dermal fibroblasts (NDFs), human mesenchymal stem cells (MSCs), human melanocytes and human immune cells (T-cells) were frozen in the solution with different concentration of DMSO and sucrose. The results were shown in FIGS. 3A to 3F. Increasing DMSO concentration brings the decrease of mechanical property of ice MNs. In one preferable embodiment, to balance the mechanical property and cell viability, the optimal formulation of freezing solution for cell delivery is the combination of 2.5 wt % DMSO with 100 mM sucrose.

Figures 4A, 4B:
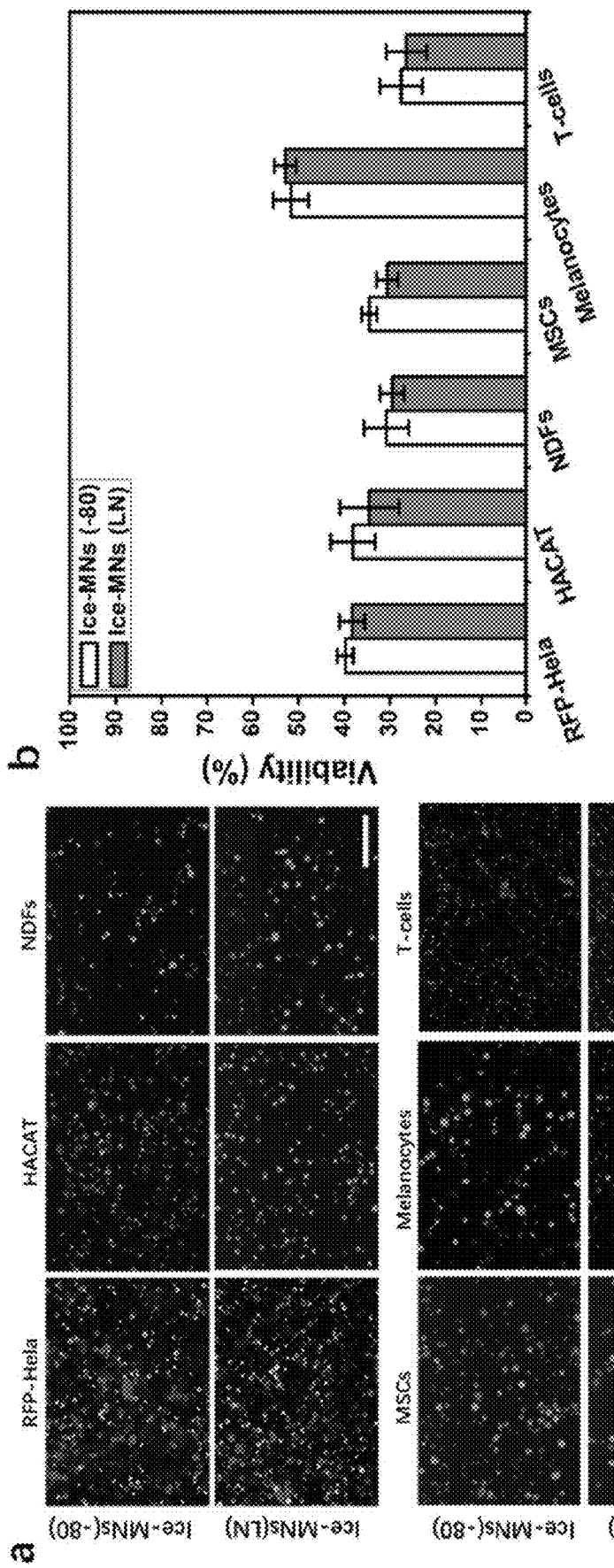
Figure 5A:
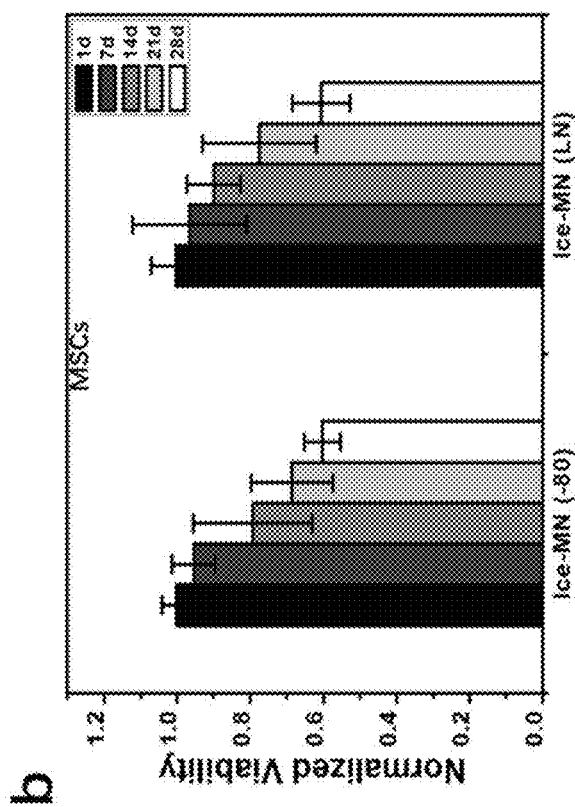
FIG. 5A to 5C are plots showing the viability of RFP-Hela (a), MSCs (b) and melanocytes (c), respectively, after recovering from ice-MNs (−80° C.) and ice-MNs (LN) for long-time storage.
Figure 5B:
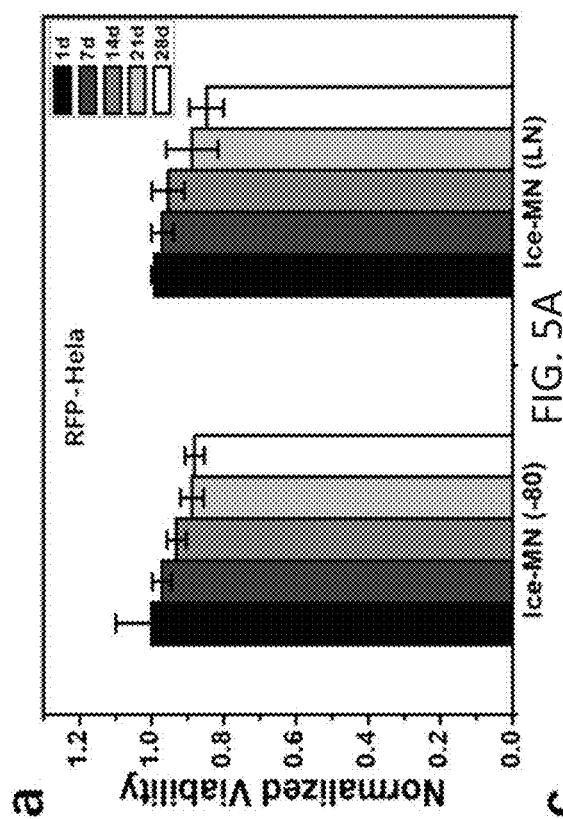
Figure 5C:
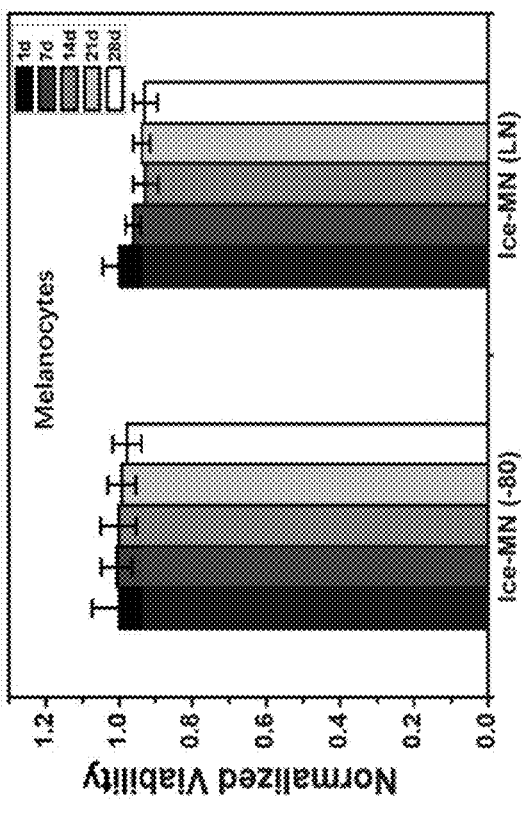

Furthermore, with reference to FIGS. 4A and 4B, the six types of cells were integrated in ice MNs and stored at freezer (−80° C.) and LN for 1 day. All types of cells maintained about 30% viability after 1-day storage. In addition, the viability of RFP-Hela, MSCs and melanocytes that were loaded in ice-MNs (−80° C.) and ice-MNs (LN) for long time storage were also tested. Referring to FIGS. 5A to 5C, it shows that cells could still maintained alive after being stored for 28 days.

Figure 6D:
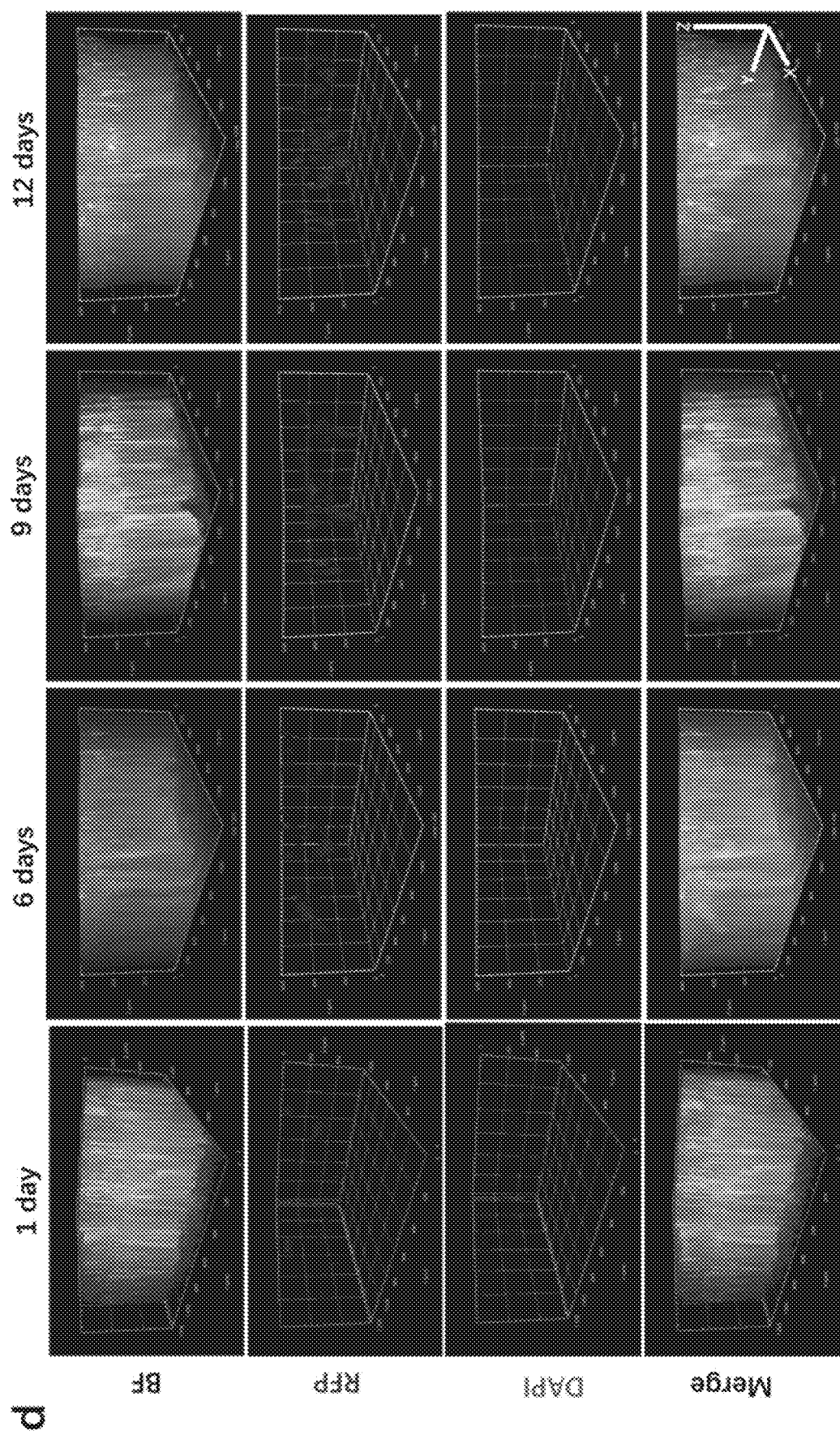

For the following experiment, the RFP-Hela loaded ice-MNs (LN) were selected as studying group and directly used after 1-day storage. The ice-MNs can successfully deliver the RFP-Hela into 3D hydrogel system (fake skin model) and the alive RFP-Hela could proliferate in this system, as shown in FIG. 6.

Figure 7B:
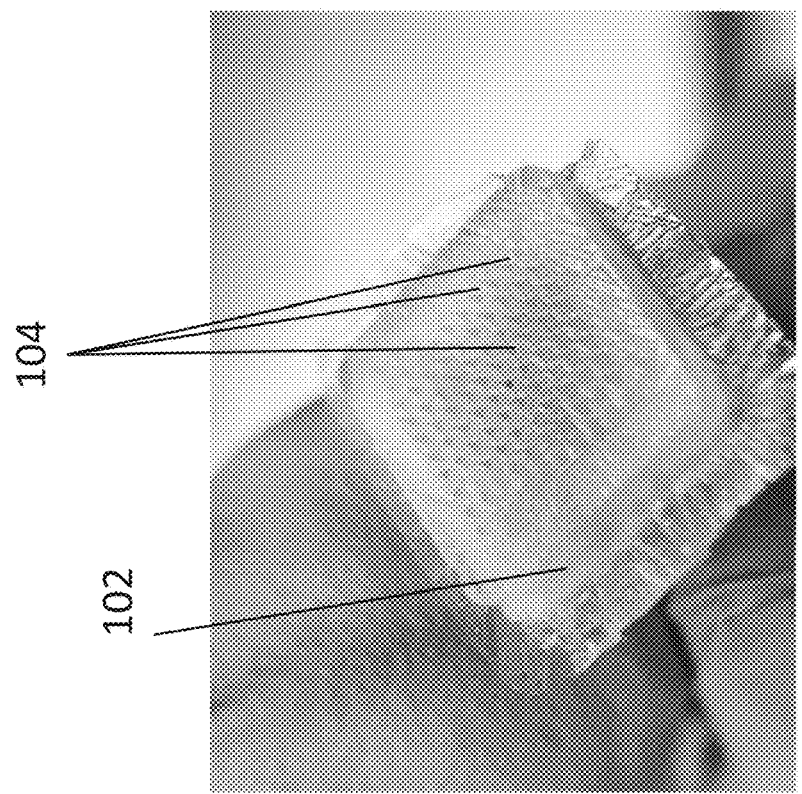
FIGS. 7A and 7B are images showing a cryo formulation-based microneedle device in accordance with an embodiment of the present invention, in which the microneedle device is attached to a handle.
Figure 7A:
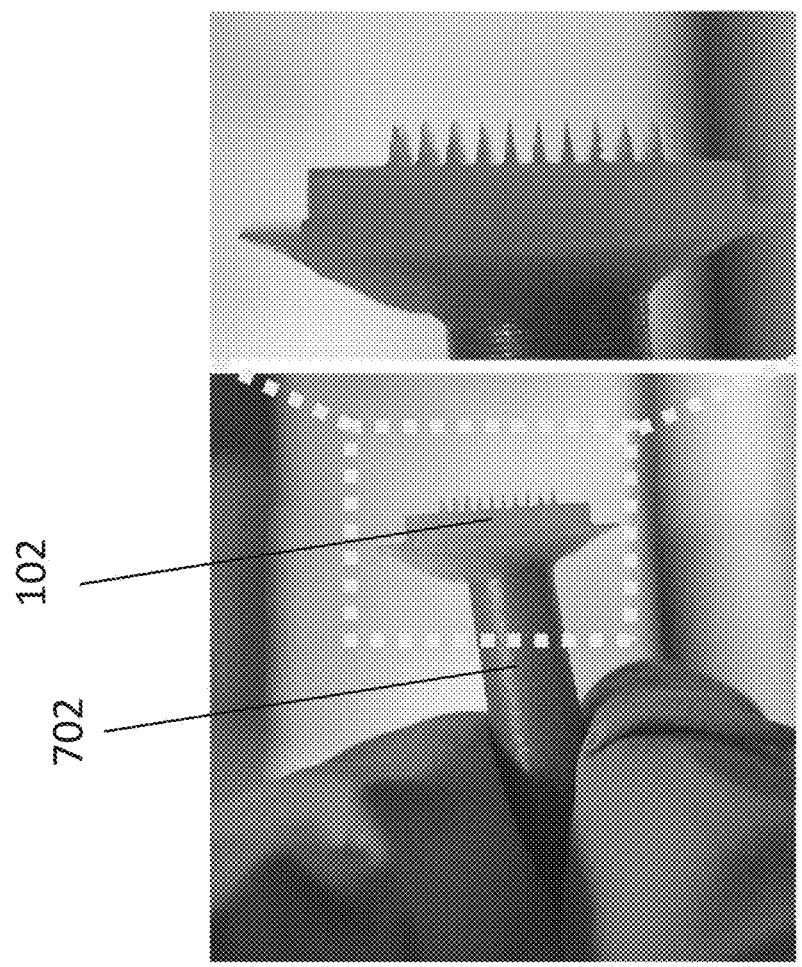

With reference to FIGS. 7A and 7B, there is shown an embodiment of using the microneedle device 100 as described earlier, for example to deliver a certain dosage of RFP-Hela to mice using the MN patches 102. The method comprises the step of: removing the microneedle device 100 from a storage place; and applying the microneedle device 100 within a predetermined period of time, such as 30 seconds, after removal from the storage place.

Preferably, the microneedle patches 102 are arranged to facilities a predetermined penetration depth, such as 50-1000 μm, of the bioactive therapeutic agents into the skin.

Optionally, the method further comprises the step of temporally attaching the microneedle device 100 to a handle 702, thereby allowing an operator to apply the microneedle device 100 by holding the handle 702. For example, referring to FIGS. 7A and 7B, a rod shape handle 702 may be attached to the base of the MN patch 102 by using suitable binder, such that the operator of the patch 102 may hold the handle 702 with his thumb and index finger to apply the patch to the skin to a desired target spot, followed by removing the handle 702 from the base of the patch 102 after successfully deploying the patch 102 on the skin surface with the MNs 104 penetrating the skin surface.

In addition, an animal experiment was conducted to evaluate the performance of the apparatus fabricated in accordance with embodiments of the present invention. The RFP-Hela loaded ice MNs can easily penetrate into mice skin by the thumb force. It is clear that there was no harm effects of ice MNs on mice skin as show in FIGS. 8A to 8D, except for the microholes created by the MNs. It was also observed that the holes gradually disappeared after 10 mins as shown in FIG. 8D.

Furthermore, the ice MNs may be applied in clinic applications. The inventors monitored the intensity red fluorescent protein secreted by the delivered RFP-Hela. It demonstrated that the RFP-Hela could survive in mice skin and continued to secrete RFP after being delivered into mice skin by ice MNs as shown in FIGS. 9A to 9C. Alternatively, the ice microneedles may be used for cell delivery.

These embodiments may be advantageous in that, the ice-based MNs may be used in various treatments of skin diseases and facelift by delivering all kinds of drugs and biologics. Example applications include the treatment such as (but not limited to) vitiligo, melanoma, skin regeneration, wound healing, hair regeneration, and anti-wrinkling.

Advantageously, the MN-based device may be applied for loading and transdermal delivery of various types of bioactive therapeutic agents (e.g. therapeutic cells, small molecular drug, proteins/peptides, DNA/RNA, bacteria, virus, fungi, et al.) in a minimally-invasive manner. This device can maintain the viability and bioactivity of loaded therapeutic agents. The device has enough mechanical strength, which ensures the device can penetrate across the stratum corneum and deliver the cargo into the targeted skin layers.

By selecting and loading certain therapeutic agents, the devices can be applied for different biomedical applications, such as cancer immunotherapy (by loading dendritic cells or T cells), treatment of vitiligo (by loading melanocytes), treatment of diabetes (by loading insulin or insulin-secreting cells), treatment of topical infection (by loading probiotic bacteria or bacteriophages) and promoting skin regeneration (by loading fibroblasts or stem cells).

Embodiments of the present invention may also provide the following advantages.

Firstly, the materials of present MNs are aqueous solutions which are readily accessible and easy to prepare. For example, the 2.5% wt DMSO in water or PBS and 200 mM sucrose dissolved in water or PBS. This is different from other MN devices usually made from polymer, metal, silicon and glass, which might involve with expensive raw materials, complex chemical synthesis and potential issue of biocompatibility.

Second, the fabrication process of the device is simpler, compared with the fabrication of solid or hollow MNs.

Third, this present invention integrates living cells into MNs as a ready-to-use device and the cells can maintain alive inside the device for a long-term storage. By harnessing the device according to the embodiments of the present invention, the transdermal delivery of cells can be easily performed without assistance of any extra device. Therefore, application processes can be greatly simplified. This is particularly different from other technologies or example devices for cell delivery which may involve complex and redundant procedures including cell harvest and preparation of cell infusing solution during each administration processes, or may require additional equipment for providing infusion pressure.

Forth, the microneedle patches can also be applied for loading and delivery of many types of bioactive therapeutics, such as drugs, protein/peptides, nucleic acid, virus and bacterial, et al, for different biomedical purposes, which is different from other examples that only focus on a single type of therapeutics.

In some embodiments, the microneedle patches may be applied for topical delivery of predator bacteria to treat ocular bacterial infections. With reference to FIGS. 10 to 22, there is shown alternative embodiments of the present invention, in which the cryo formulation-based microneedle device is used for ocular delivery of bioactive therapeutic agents. Instead of applying the MNs patches on a skin surface of a target, the microneedle patch is adapted to be applied on cornea of an eye, in which the miniaturized needles penetrates into the eye; and the miniaturized needles is further arranged to melt so as to release one or more bioactive therapeutic agents into the eye to achieve a targeted therapeutic effect.

The inventors, through their own research, trials and experiments, devised that bacteria may be the major etiological agents in ocular infections. If left untreated, they can damage the structures of the eye leading to irreversible visual impairments and blindness.

Without wishing to be bound by theory, eye infections may be treated with antibiotic eye drops. However, the abuse of antibiotics leads to evolution of antibiotic-resistant bacteria, which further affect antibiotics-based treatments. Alternatively, predatory bacteria such as *Bdellovibrio bacteriovorus* (*B. bacteriovorus*), may be used to reduce *Klebsiella pneumoniae* bacterial burden, which therefore may be used to accelerated the clearance of pathogens from the ocular surface.

For example, ocular delivery of predatory bacteria may be performed topically through topical instillation. This may be suitable for the treatment of external infection such as conjunctivitis and keratitis, however, it may lose effectiveness for internal infection like endophthalmitis that requires the migration and deep penetration of the predatory bacteria. Alternatively, intravitreal injection can be performed, such as using microneedles (MNs) in accordance with embodiments of the present invention. Advantageously, these tiny needles allow the precise control of the injection depth and area.

Figure 10:
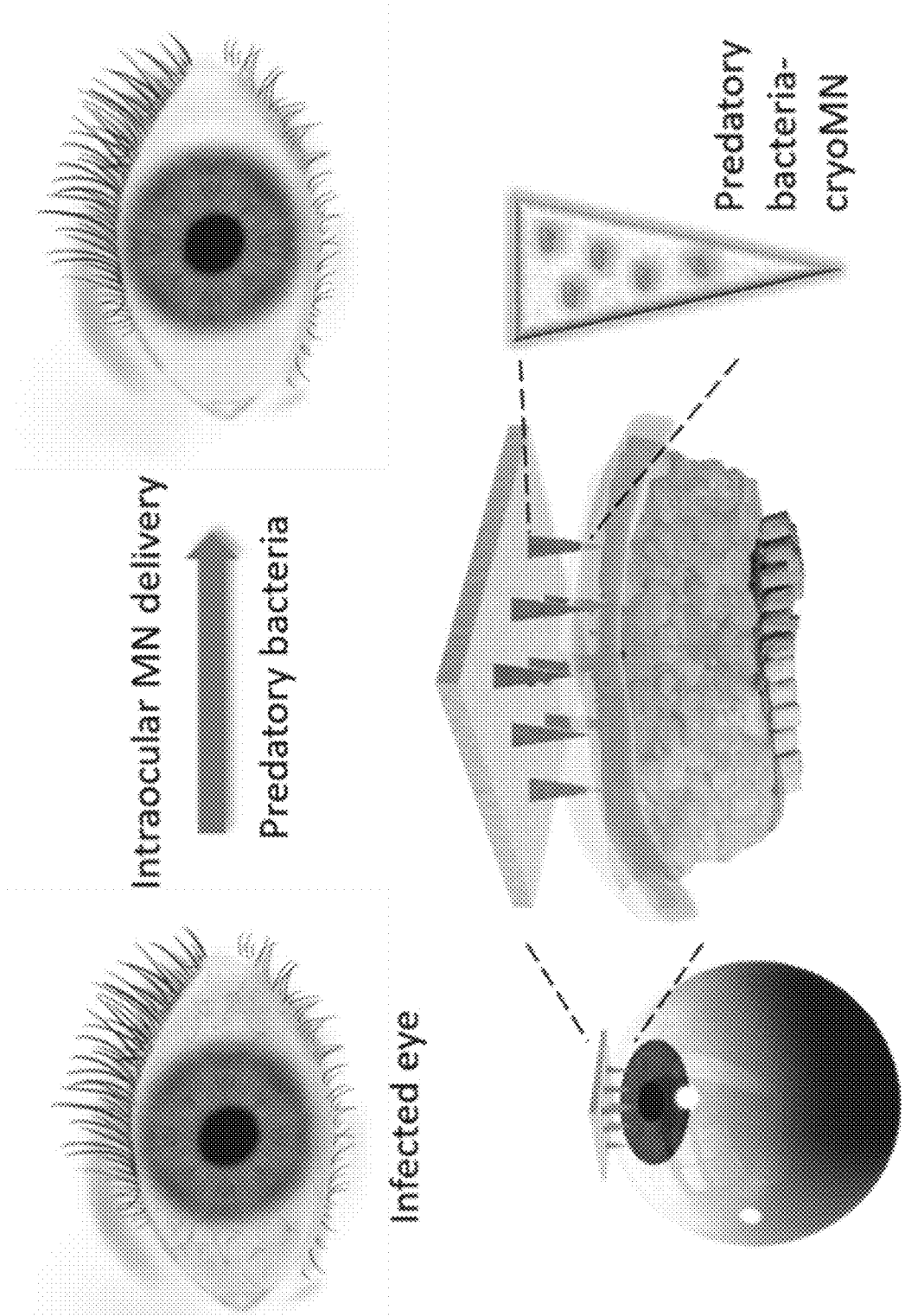
FIG. 10 is an illustration of cryoMNs for ocular delivery of predatory bacteria in treating eye infection using the microneedle device in accordance with an embodiment of the present invention.

Preferably, with reference to FIG. 10, cryoMNs may be fabricated to package and for delivering predatory bacteria for eye infection treatment. Taking *B. bacteriovorus* as the model predatory bacteria, the cryoMN may include a formulation to maximize bacterial viability while maintaining their mechanical properties for cornea penetration. The inventors also performed in vitro experiments to evaluate the retention of predatory ability of *B. bacteriovorus* post the release from cryoMNs against gram-negative bacteria. Four distinct gram-negative bacteria were studied in the experiments, namely *Escherichia coli* (*E. coli*), *Pseudomonas aeruginosa* (*P. aeruginosa*), *Acinetobacter baumannii* (*A. baumannii*), and *Klebsiella pneumoniae* (*K. pneumoniae*). These bacteria were chosen for their clinical significance. *E. coli* may induce conjunctivitis or dacryocystitis. *P. aeruginosa* and *A. baumannii* are responsible for keratitis resulted from trauma, contact lens wear or ocular surgery. Meanwhile, *K. pneumoniae* may spread from the blood and cause endophthalmitis. Finally, the therapeutic effect of the cryoMN formulation was demonstrated in the mouse eye infection model (*E. coli* as the pathogen), taking the topically applied *B. bacteriovorus* as the control.

To perform these experiments, Lysogeny broth (LB) agar, agarose, glycerol, calcium chloride, magnesium chloride, polystyrene (PS), polycaprolactone (PCL), polylactic acid (PLA) and paraformaldehyde were obtained from Sigma-Aldrich (Singapore). Mini hyaluronic acid (miniHA) powder was bought from Bloomage Freda Biopharm Co. Ltd (China). Phosphate buffer saline (PBS), 4-(2-hydroxyethyl)-1-piperazineethanesulfonic acid (HEPES) were purchased from GE Hyclone (Singapore). FM™ 4-64FX dye was purchased from Thermo Fisher scientific (Singapore). Nutrient Broth and LB were bought from BD Diagnostics (USA). *B. bacteriovorus* (ATCC® 15143™), *E. coli* (ATCC® 25922™), *E. coli* (ATCC® 10536™, only for *B. bacteriovorus* culturing), *P. aeruginosa* (PAO1-GFP), *A. baumannii* (ATCC® 19606™), and *K. pneumoniae* (ATCC® BAA-2784™) were purchased from ATCC (USA).

*E. coli* (ATCC10536) were grown in LB broth with aeration at 37° C. and harvested during stationary growth phase. *B. bacteriovorus* were grown and maintained using *E. coli* as the prey. They were maintained as plaques in double-layered diluted nutrient broth, a 1:10 dilution of nutrient broth supplemented with 2 mM $CaCl_2$ and 3 mM $MgCl_2$ and agar (0.6% agar in the top layer and 1% agar in the bottom layer, pH=7.2). Lysates were initiated by co-culturing a plug of top agar containing *B. bacteriovorus* with washed prey/host cells (*E. coli* ATCC10536) in HEPES buffer. They were incubated at 30° C. on a rotary shaker until the culture cleared (stock-lysates). To obtain higher predator concentrations, fresh predator cultures were obtained as previous reports. Briefly, 2 ml of washed overnight culture prey cells (~$1\times10^9$ CFU/ml) were incubated with 2 ml of stock-lysates in 20 ml of HEPES. The co-cultures were incubated for 24 h before passing three times through a sterilized 0.45 mm Minisart® syringe filter (Sartorius) to remove any remaining prey cell and debris to purify the predators. Next centrifugation was conducted 3 times at 15,000 rpm for 30 mins to concentrate the predator cells. For the last wash, the pellet was re-suspended in 2 ml PBS solution to reach a final absorbance of ~0.3-0.4 at 600 nm. The final concentration was determined by double-layered agar method each time. 50 µl aliquots of the predator samples were plated on LB agar and cultured at 37° C. to confirm thorough removal of prey cells.

Figure 11:
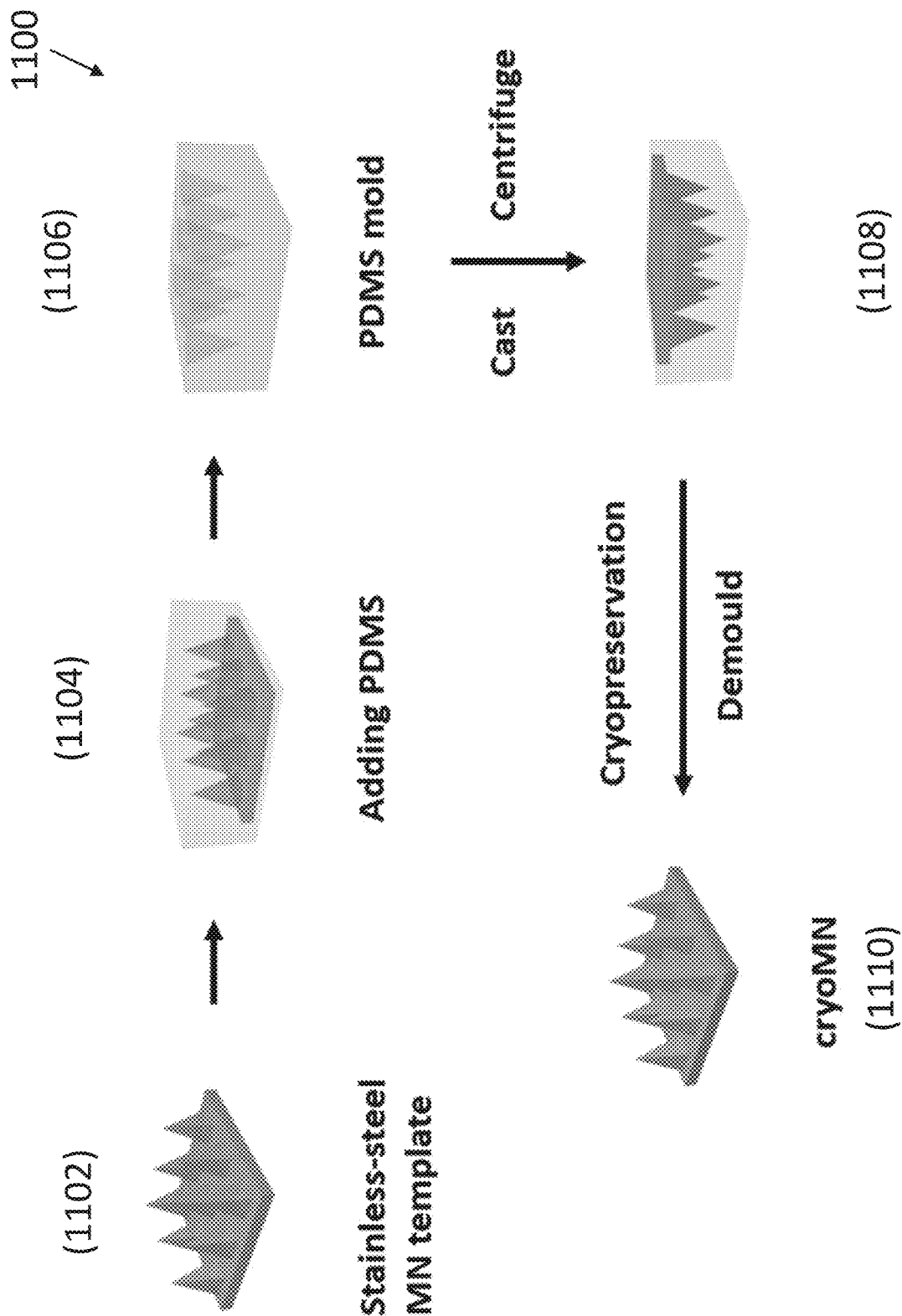
FIG. 11 is an example fabrication process of the microneedle device for treating eye infection in accordance with an embodiment of the present invention.

Preferably, referring also to FIG. 11, the cryoMNs may be fabricated through template molding, in which the PDMS mold is a negative mold which may be obtained by replicating the metal mold which a positive template defined with a predetermined pattern of the array of microneedle structures. The fabrication process 1100 starts at step 1102 where a stainless-steel MN template defined with the necessary patterns is provided, followed by step 1104, PDMS is added or coated on the stainless-steel MN template, and then at step 1106, a negative PDMS mold may be obtained after curing of PDMS material and detaching of the positive template from the PDMS mold.

At step 1108, buffer solution containing predatory bacteria may be cast into the PDMS negative mold that was made from a designed stainless-steel MN template. The buffer solutions for preparing cryoMNs were composed of PBS, glycerol, and predatory bacteria. The concentrations of glycerol ranged from 0% to 20%. The concentration of bacteria ranged from $10^8$ PFU/ml to $10^9$ PFU/ml. 50 µl of optimized formulation containing *B. bacteriovorus* was added to the PDMS negative mold and centrifuged at 4000 rpm for 1 min, driving the solution into the tip cavities. 20 µl solution was then added as the base for 3×3 MN mold. The whole system was cooled at 4° C. for 30 mins to allow the sedimentation of bacteria from the base, concentrating the bacteria in the MN tips. They were then kept at −20° C. for 4 h prior prolonged storage of the fabricated MNs at −80° C. Finally, at step 1110, the cryoMN patches can be peeled off from the molds after 4 h storage at −20° C.

In the experiment, the inventors performed following tests to evaluate the physical/biochemical performance of the fabricated MNs, including:

Mechanical test: The mechanical strength of cryo-MN patch was evaluated by compression test using the Instron 5543 Tensile Meter. MN patch was placed on the flat stainless-steel platen with tips facing upward. Subsequently, vertical force was applied to tips with a constant speed of 0.5 mm/min. The displacement vs loading force curve was recorded until a preset maximum force of 4 N/needle was achieved.

In vitro predation experiment: The predatory ability of *B. bacteriovorus* was examined through co-culturing with gram-negative bacteria (*E. coli* (ATCC25922), *P. aeruginosa* (PAO1-GFP), *A. baumannii*, and *K. pneumoniae*) in vitro. Briefly, co-cultures were prepared by adding 0.1 ml of HEPES washed prey cells (~$1\times10^8$ CFU/ml) to 0.1 ml of harvested predators to compare their susceptibility to predation. The cultures were incubated at 30° C. for 48 h. Optical density at 600 nm was recorded throughout the co-culture process by BioTek plate reader. Prey ability was evaluated by the reduction of prey cell number after the co-culture. Cell viability was quantified by CFU enumeration following dilution plating at 0, 24 and 48 h. Each experiment was conducted thrice in triplicate.

Cornea penetration analysis: cryoMN patch was thumb pressed into 0.4% agarose gel or porcine cornea. Agarose gel was prepared by mixing agarose powder with ultrapure water under heat until it was completely dissolved. Porcine eyes were taken from 6 to 7 months old pigs and collected from Primary Industries Pte Ltd (Singapore). Post MN penetration; agarose gel was imaged using confocal microscope Zeiss LSM 800. The appearance of porcine cornea was recorded by microlens-equipped digital camera. MN-treated porcine cornea was fixed with 4% paraformaldehyde for cryo-sectioning and stained with Hematoxylin and Eosin (H&E) for histological analysis.

Ocular delivery of predatory bacteria with cyroMNs in the eye infection mouse model: The antimicrobial efficacy of predatory bacteria as topical eye drops and incorporated in MN along with untreated control were assessed in a mice model of *E. coli* keratitis. Twelve pathogen free 6-8 weeks old male mice (wild type C57BL/6) as per the SingHealth Institutional Animal Care and Use Committee (IACUC) guidelines (Protocol No. 2016/SHS/1204) were used. For the animal experimentation, all the animals were handled as per the guidelines of Association for Research in Vision and Ophthalmology (ARVO). Mice were distributed into 3 groups randomly. Group I was treated with 0.9% NaCl topically, Group II was treated with *B. bacteriovorus* solution topically and Group III was treated with *B. bacteriovorus*-containing cryoMN patches. *E. coli* (ATCC25922) was grown overnight in Tryptic Soy Agar (TSA) plates at 37° C. Isolated single bacterial colonies were picked up and suspended in sterile saline at the concentration of $1\text{-}5 \times 10^6$ CFU/mL. Prior to the infection procedure, eyes of mice were examined by slit-lamp photography and Optical Coherence Tomography (OCT) to ensure no corneal aberration (i.e. vascularization or other ocular defects). Mice were anesthetized by an intraperitoneal injection of xylazine (10 mg/kg, Troy Laboratories, Smithfield, Australia) and ketamine (80 mg/kg, Ketamine, Parnell Laboratories, Australia) under the dissecting microscope (Zeiss, Stemi-2000 C). One drop of 1-5% lidocaine hydrochloride was topically applied as anesthesia instilled before corneal wounding, and the corneal epithelium was then scratched using a sterile Beaver6400 Mini-Blade to create a superficial wound without damaging the stroma. Next, the cornea was irrigated with sterile saline to wash away any debris and residual topical anesthetic agent. After which, 15 μL bacterial suspension containing $1\text{-}5 \times 10^6$ CFU/mL of *E. coli* (ATCC 25922) were applied topically on the corneal surface. 6 h post the infection, mice were treated with 0.9% NaCl, *B. bacteriovorus* solution or cryoMNs containing *B. bacteriovorus* topically three times per day for 3 days, with 3 h interval between each application. Mouse eyes were then examined daily by slit lamp and OCT.

Quantification of viable bacteria in the mouse cornea: At day 4, the mice were sacrificed, and their eyes were enucleated for bacterial quantification. The mouse corneas were dissected and individually homogenized in sterile PBS by Pellet pestles cordless motor (Z359971, Sigma) with sterile plastic pestles. The homogenization was conducted with the help of bead beating using sterile glass beads (2 mm). The resulted solution was diluted with sterile saline to give $10^{-1}$, $10^{-2}$, $10^{-3}$, $10^{-4}$, and $10^{-5}$ dilutions. 0.1 mL of each suspension was inoculated onto TSA plates in duplicate. The plates were incubated at 37° C. for 24 h before the numbers of colonies were counted. The results were expressed as the logic number of CFU/cornea.

Figure 12:
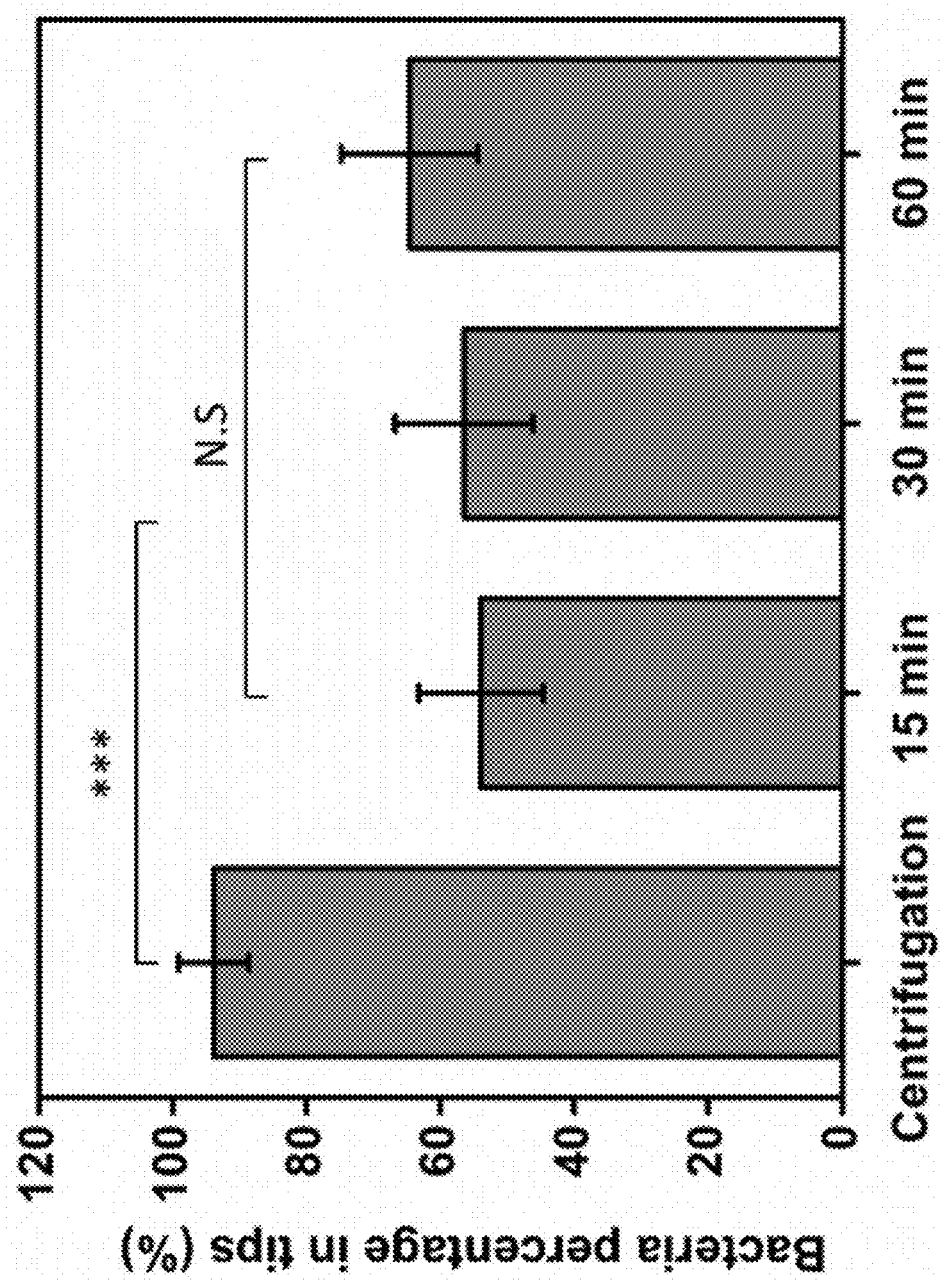
FIG. 12 is a plot showing a comparison of percentage of bacterial inside needle tips by either centrifugation or natural sediment.

In this example, the original stainless-steel template had a 3×3 MN array with inter-needle spacing of 450 μm. Each MN tip displayed a height of 600 μm with a base width of 250 μm. This design has been shown to fit the size of mouse cornea, and accordingly, PDMS negative mold was derived from this master template and used for preparing cryoMNs as described earlier. The cryoMN formulation was composed of 5% sterile glycerol and *B. bacteriovorus* with the concentration from $1 \times 10^8$ to $1 \times 10^9$ PFU/mL. When the solution was loaded into the PDMS mold, low-speed centrifugation was performed to load bacteria into the tip cavities. Alternatively, sedimentation may be used, however, without centrifugation, it would need more than 60 mins to get 60% seeded bacteria into the tips through gravity, referring to the plot as shown in FIG. 12.

Figure 13B:
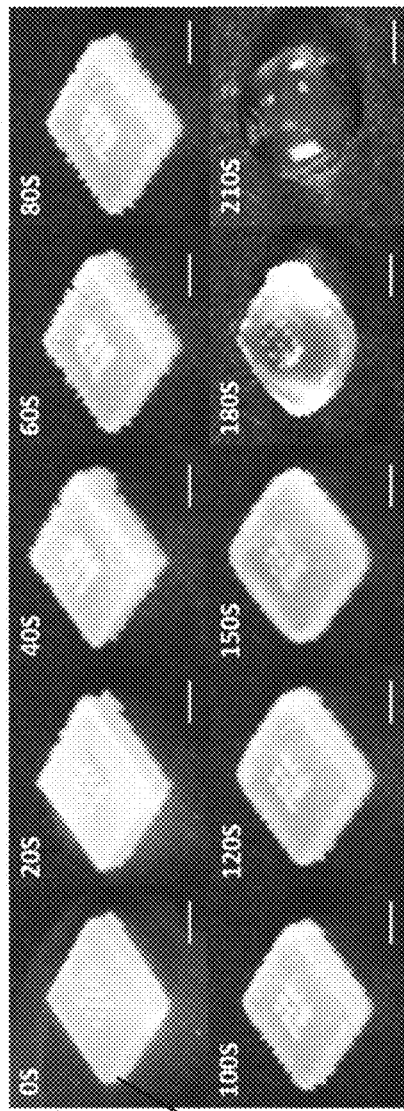
Figure 13A:
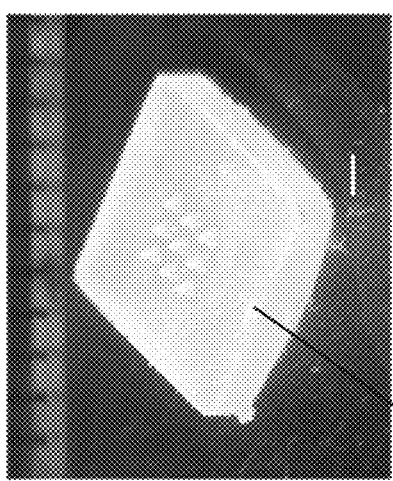
Figure 13D:
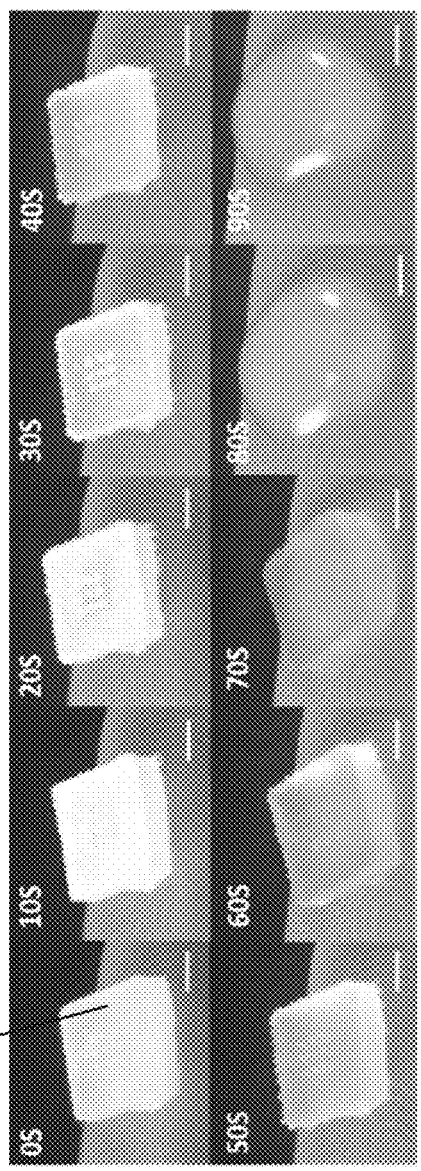
Figure 13C:
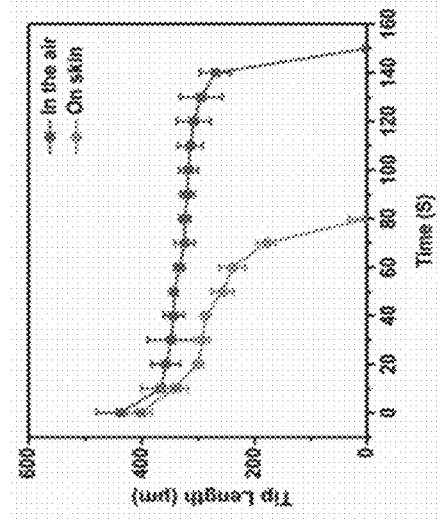
Figure 14:
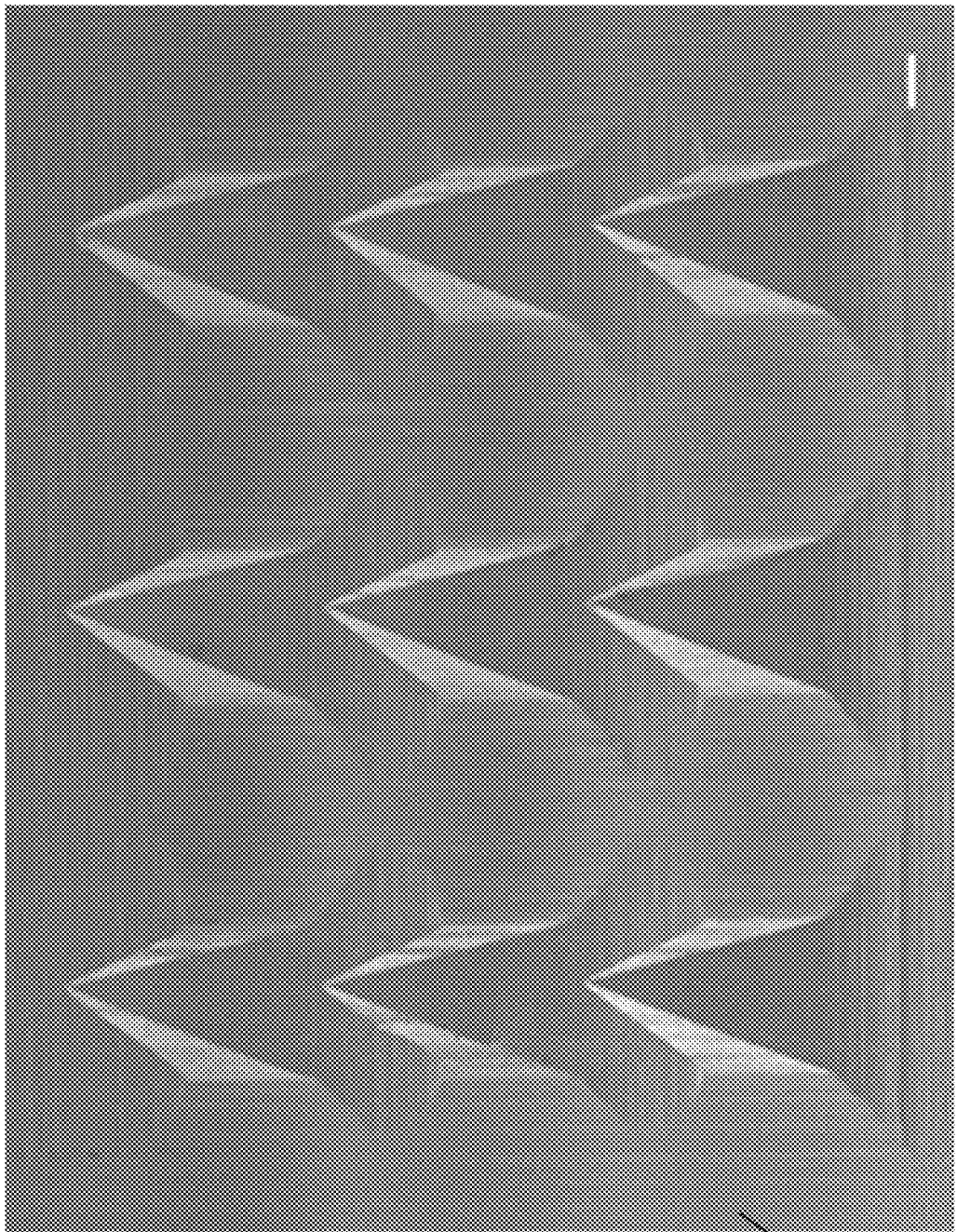
FIG. 14 is a scanning Electron Microscope (SEM) image of stainless-steel microneedle (MN) mother template (scale bar is 100 μm)

With reference to FIG. 13A, after the freezing process, the cryoMNs 1302 were peeled off from the PDMS mold and showed similar morphology as the original master mold 1400 as shown in FIG. 14. Further referring to FIG. 13B, the stability of cryoMNs in both room temperature (RT, 24° C.) and body temperature was evaluated. The tip length of generated cryoMNs was roughly 400 to 440 μm. When cryoMNs were taken out from their cryopreservation environment (−80° C.) and placed under RT, frost appeared on cryoMNs in 20 s (FIG. 13C). After 150 s, the needle tips began to melt. When the cryoMNs were placed on the fingertip (37° C., FIG. 13D), the needle tips melted in 60 s. There was no pain or harsh discomfort felt during the process. Remaining needle tips were quantified and correlated with residence time to evaluate survival window of the cryoMN. As shown in FIG. 13B, cryoMNs maintained their morphology slightly longer in RT.

Figure 15B:
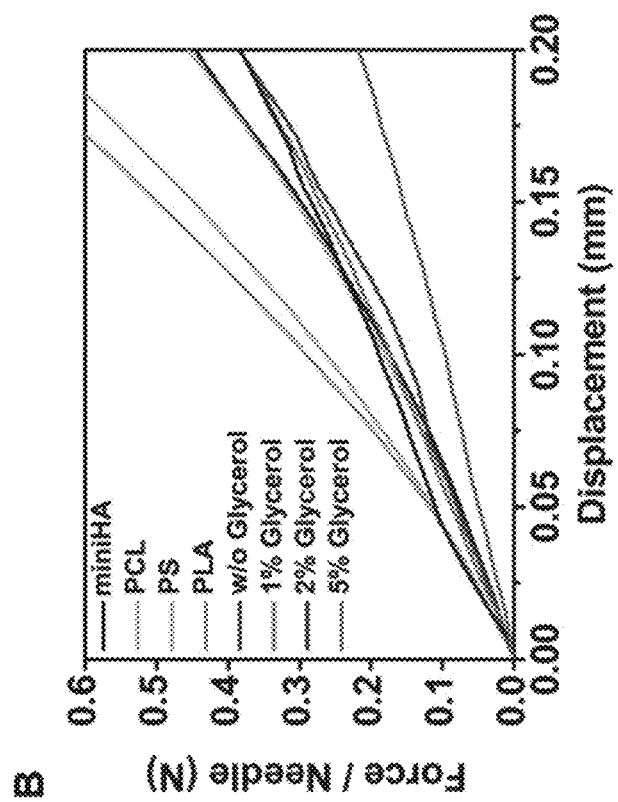
Figure 15A:
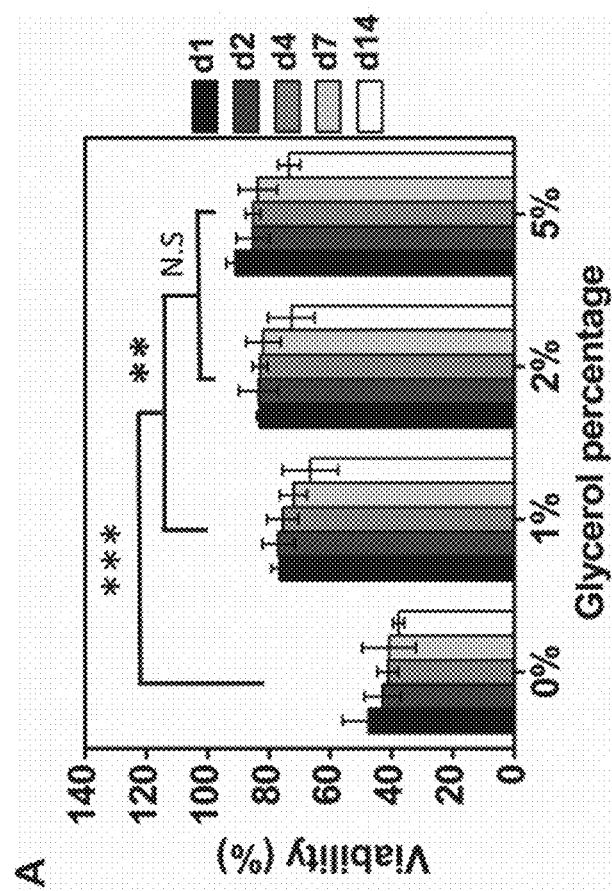
Figure 16B:
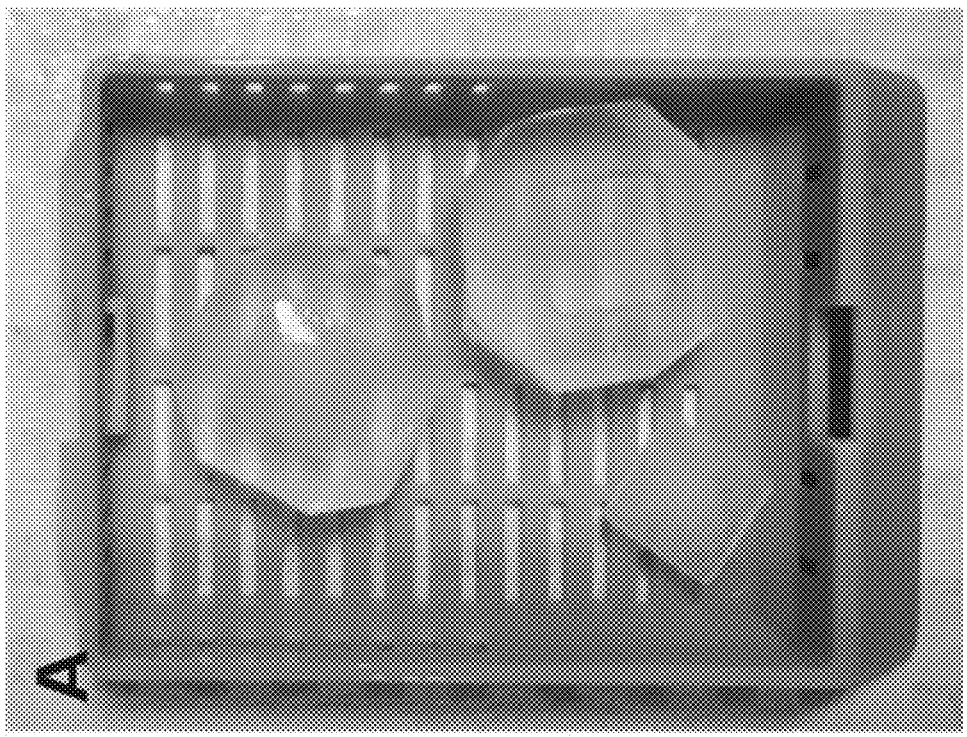
FIGS. 16A and 16B are images showing cryoMN patches made of cryoprotectant medium containing (A) 5% or (B) 10% glycerol.
Figure 16A:
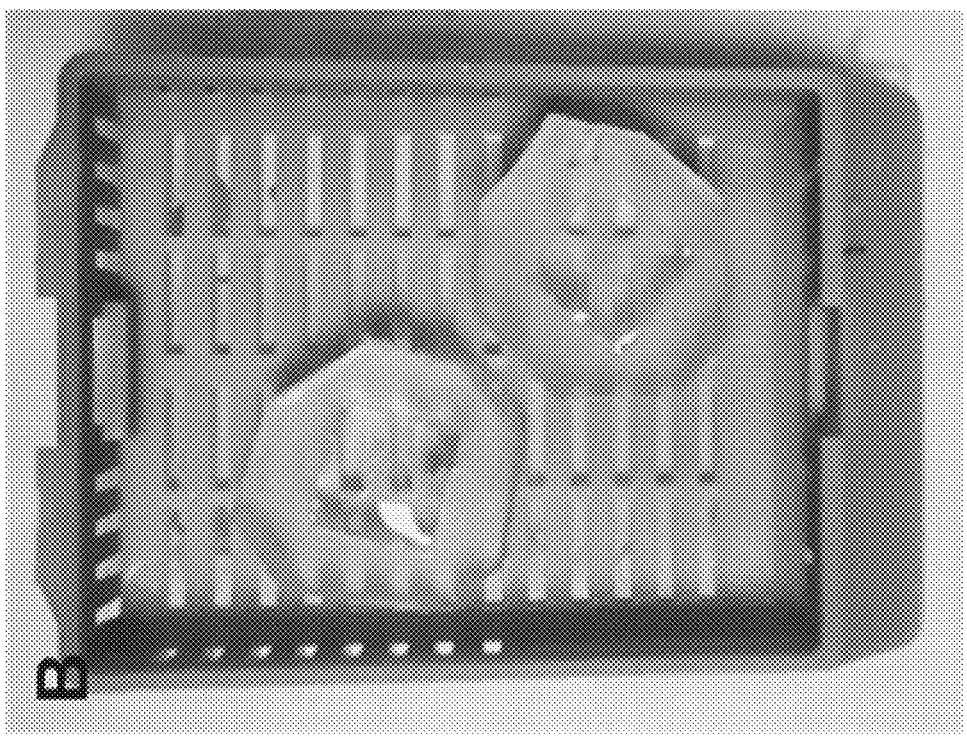

The cryoMN formulation may be optimized by tuning the glycerol concentration between 0-5%, and the inventor further examined the viability of *B. bacteriovorus* inside cryoMNs in a 14-day period post the fabrication. Referring to FIGS. 15A, without any glycerol (0%) in the formulation, the viability of *B. bacteriovorus* reduced to less than 40% through the 14 days. The addition of glycerol (1-5%) significantly improved its viability from 80% to 100%. When the glycerol concentration was more than 5%, cryoMNs became very soft and easily melt during the demolding, as shown in FIGS. 16A and 16B. Referring also to FIG. 15B, the inventors further examined the mechanical strength of cryoMNs with different glycerol concentrations and compared them with polymeric MNs made from miniHA, PCL, PS and PLA., the cryoMNs with 0%, 1%, and 2% glycerol displayed similar loading force/displacement profiles to miniHA and PCL MNs in the compression test. They could withstand a load force of 0.3 to 0.4 N per needle without fracture. Higher glycerol concentration (>5%) resulted in lower mechanical strength, but cryoMNs with 5% glycerol retained sufficient strength to penetrate through the cornea (~0.05 N/needle) In the following experiments, cryoMNs with 5% glycerol were employed.

Figure 17A:
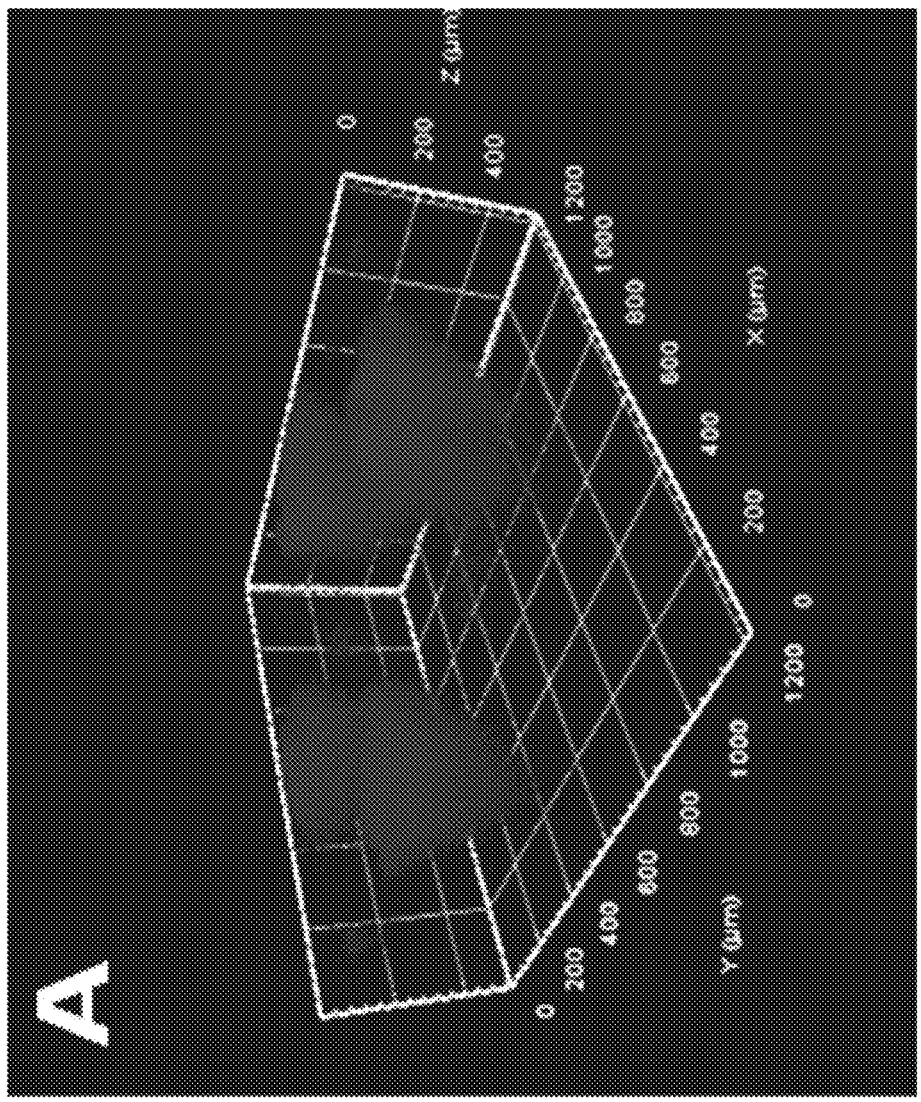
Figure 17B:
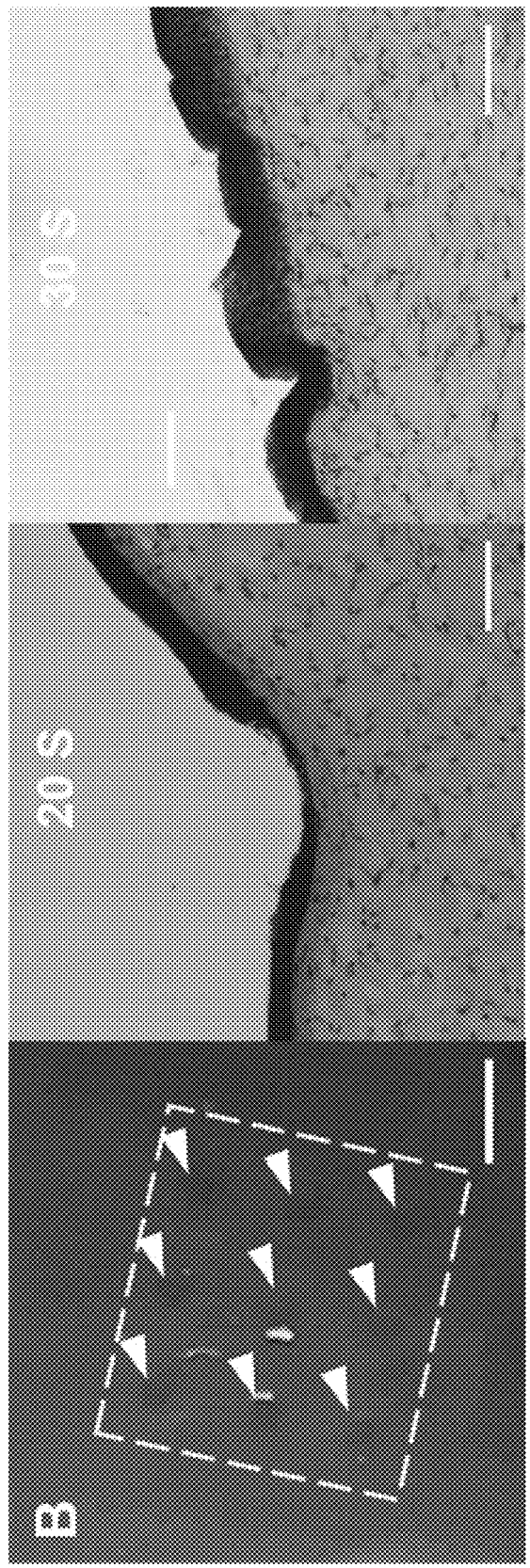

In the cornea penetration of cryoMNs test, the penetration ability of cryoMNs was firstly evaluated in agarose gel. To facilitate the imaging, cryoMNs was loaded by *E. coli* stained with red fluorophore FM™ 4-64FX. As shown in FIG. 17A, cryoMN easily pierced and delivered bacteria into hydrogel. The penetration depth was less than 400 μm, which was slightly shorter than the actual length of needles (400-450 μm).

Figure 17C:
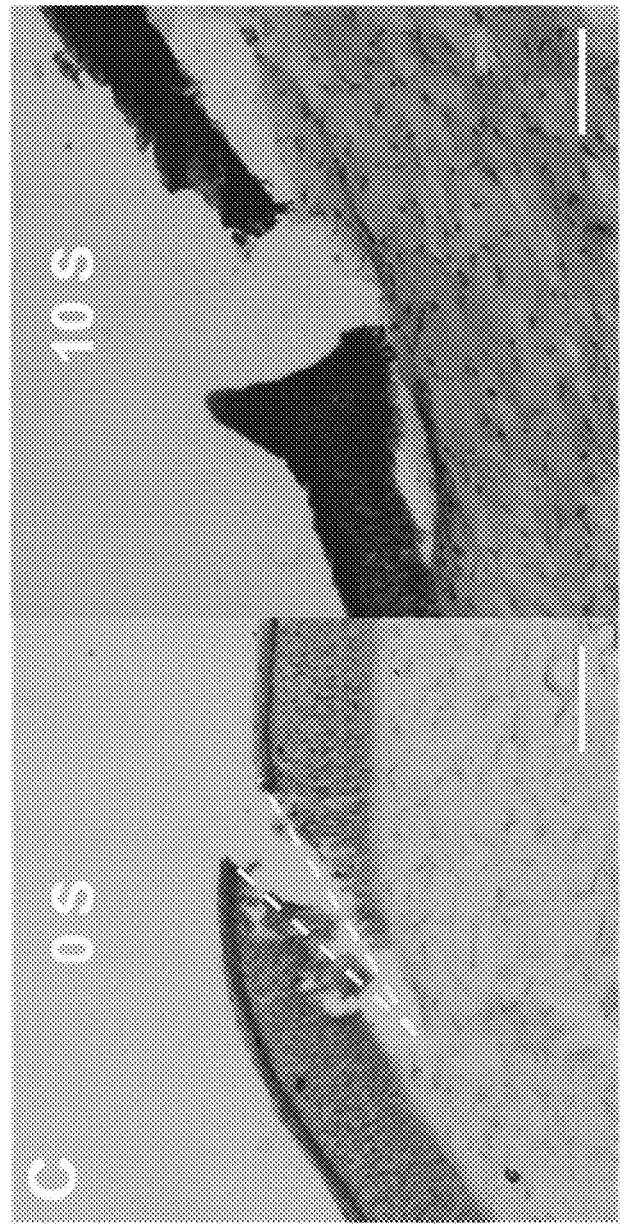
Figure 18C:
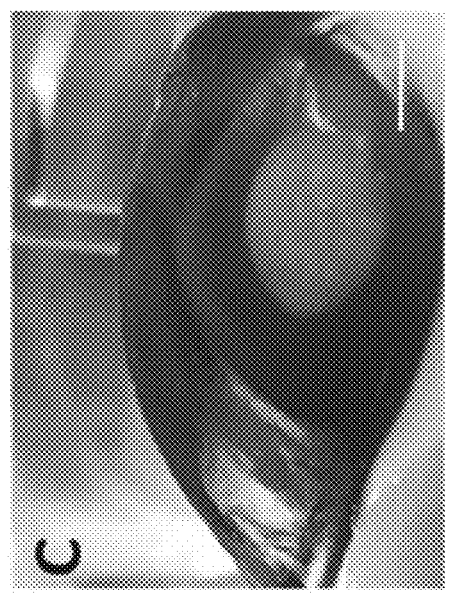
FIGS. 18A to 18C are bright-field images of the porcine eye before (A) and after (B) cryoMN insertion, and (C) a close view of the MN patterns left on the eye, respectively, in the cornea penetration tests of cryoMNs, the cryoMN patch containing 3×3 MNs was thumb pressed on the central region of porcine eye, and the scale bar is 2 mm.
Figure 18B:
Figure 18A:
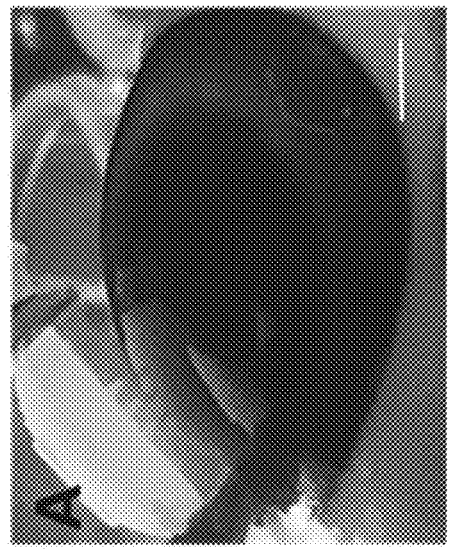

Next, cryoMNs were tested on ex vivo porcine eye, by thumb pressing into the cornea region, illustrated in FIGS. 18A to 18C. Further with reference to FIG. 17B, obvious MN pattern were observable on the eye. Tissue histology showed that cryoMN tips broke through the cornea layer (762 to 898 μm thickness as shown in FIG. 17C) and penetrated into the corneal stromal layer (~150 μm deep) which is about one third of MN height.

Figure 3A:
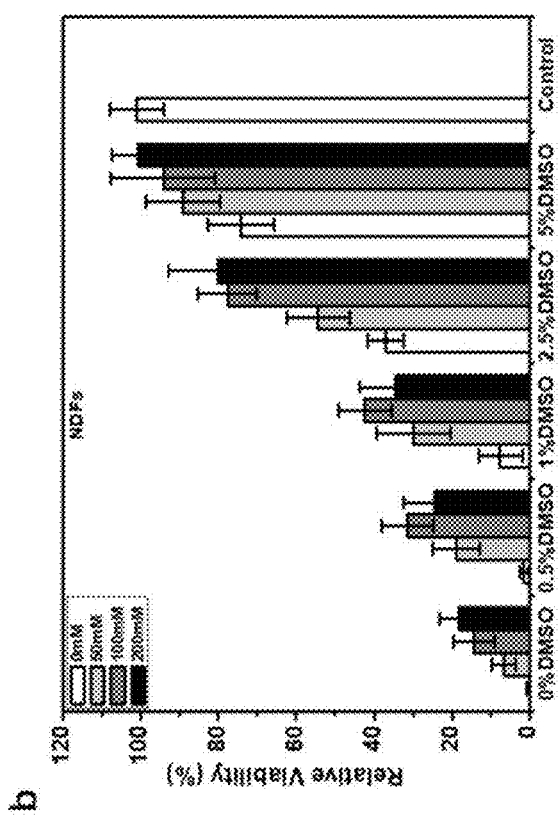
FIGS. 3A to 3F are plots showing relative viability of, RFP-Hela (a), NDFs (b), HACAT (c), MSCs (d), melanocytes (e) and T-cells (f), respectively, after being frozen in the solution with different concentrations of DMSO and sucrose at −80° C. for 1 day.
Figure 3B:
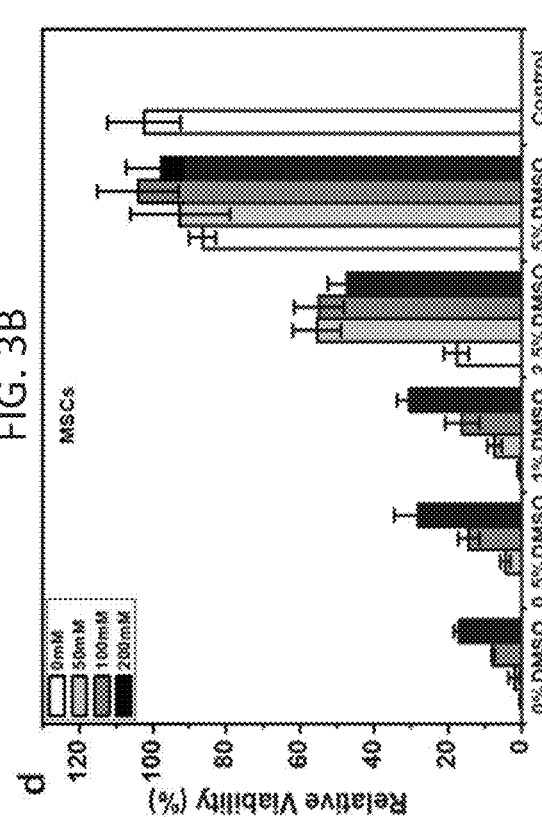
Figure 3C:
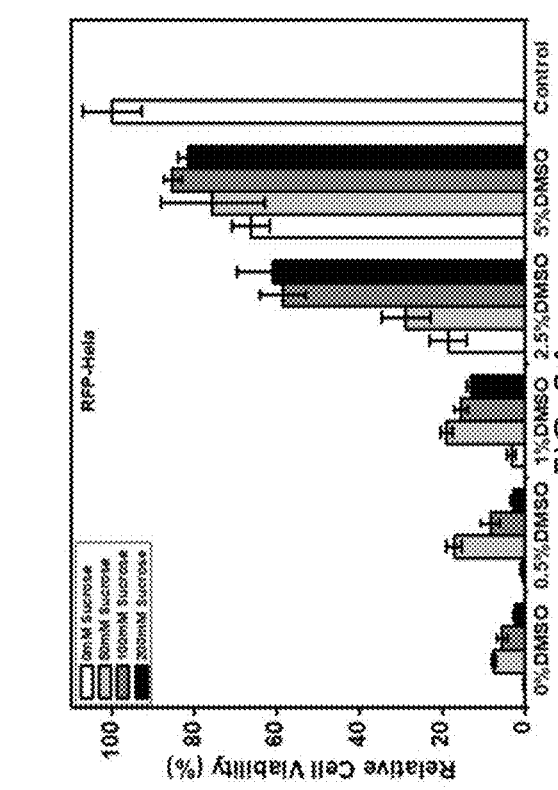
Figure 3D:
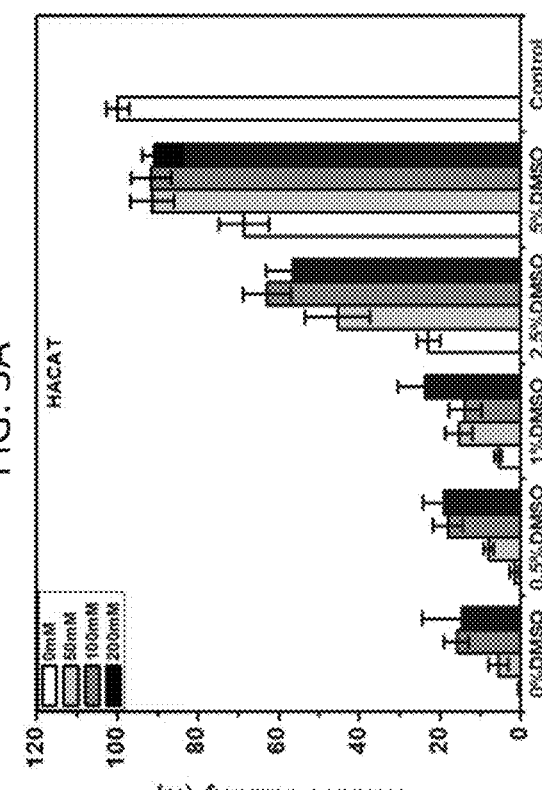
Figure 3E:
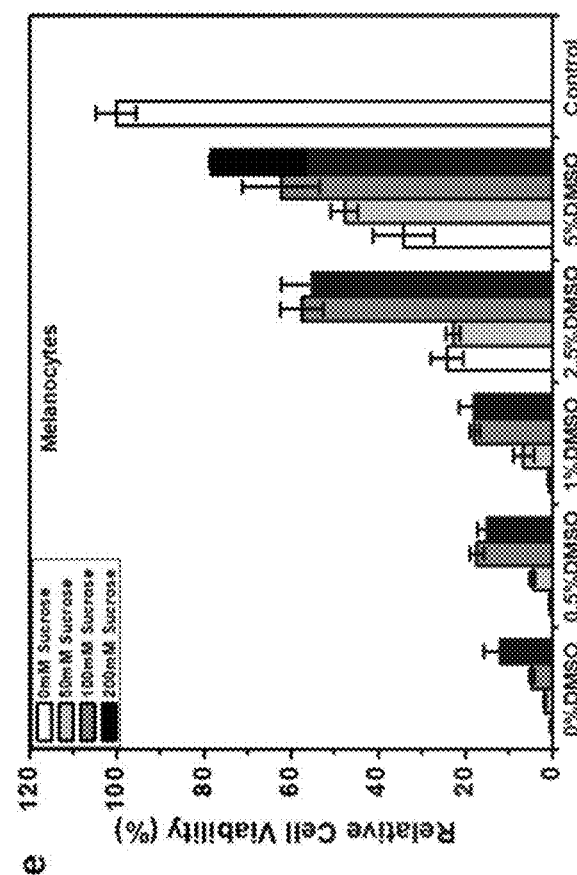
Figure 3F:
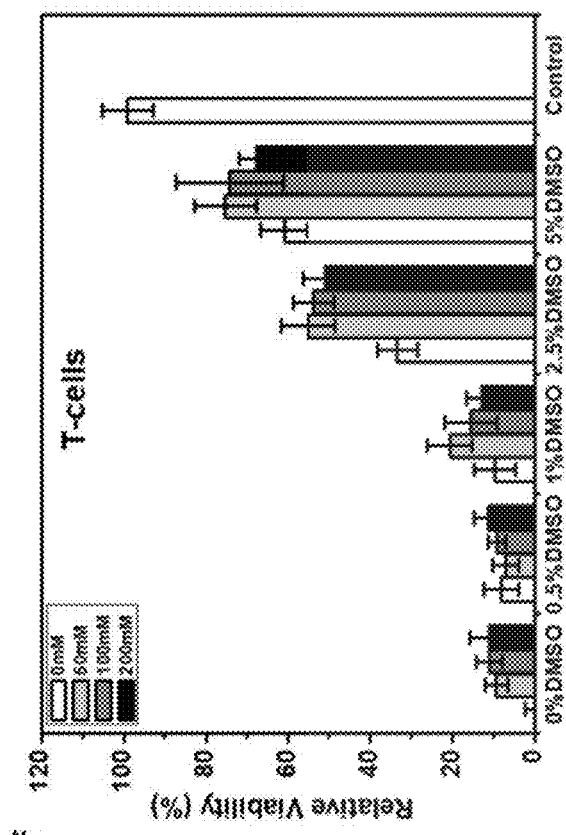

As cryoMNs undergo dissolution at RT after removal from the storage freezer (FIG. 13B), the inventors examined their cornea penetration capabilities at different time points post the retrieval. As shown in FIG. 3C, it could still penetrate the cornea layer within 10 s post the retrieval. However, the penetration ability reduced significantly when the cryoMN was left at RT for a longer duration. These results suggest that cryoMNs can be used for the bacterial delivery only if the operation times between the removal from storage and skin insertion is less than 10 s at RT. It can be expected that operation time would be longer if the operating environment temperature is lower.

Figures 19A, 19B, 19C:
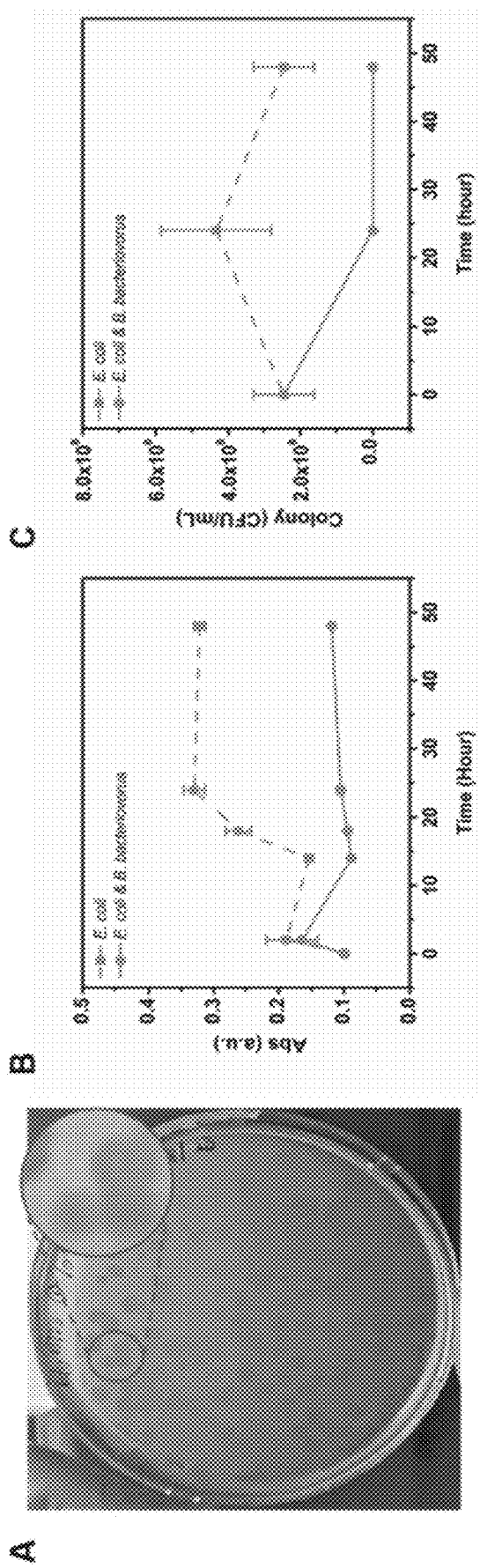

In the in vitro predation test to gram-negative bacteria, the predatory capability of free *B. bacteriovorus* against gram-negative bacteria was first confirmed with *E. coli* (ATCC25922) referring to FIG. 19A. As shown in FIG. 19B, the absorbance value of *E. coli* incubated with *B. bacteriovorus* did not increase during the 48 h period, while the absorbance value tripled for untreated *E. coli* group. This observation was corroborated by colony counting results as shown in the plot of FIG. 19C. *E. coli* concentration in the predated group decreased dramatically from 4.3×10$^8$ CFU/mL to 6500 CFU/mL within 24 h incubation, indicating a 4.8 log$_{10}$ reduction compared to untreated. The log reduction value remained similar even after 48 h suggesting no evolution of *E. coli* regrowth.

Next, with reference to FIGS. 20A to 20C, the predation efficiency of *B. bacteriovorus* following encapsulation and delivery with cryoMN patches against *E. coli* (ATCC25922), *P. aeruginosa* (PAO1-GFP) is confirmed, *A. baumannii* and *K. pneumoniae*. These pathogens are the underlying causes for the infection of eye or skin. Predation experiment was conducted by co-culturing the pathogens with predators recovered from the cryoMN. Except for PAO1-GFP, the remaining pathogens were susceptible to predation by *B. bacteriovorus*. The eradication of these pathogenic bacteria by *B. bacteriovorus* was quantified through both optical density measurement and bacterial enumeration after 48 h incubation.

The concentration change of *E. coli* without or with *B. bacteriovorus* cryoMN treatment is observed. Referring to FIG. 20A, the optical density of *E. coli* steadily increased in the untreated *E. coli* only group, while dramatic decrease was observed in the co-culture predated group. Further referring to FIG. 20B, colony changes showed a similar trend to that of absorbance reading, with 4 log$_{10}$ reduction observed in the co-culture predated group. Representative photographs of agar plates for control and co-culture group after 48 h are shown for better clarity. As shown FIG. 20C, there was complete clearance of bacterial colonies in co-culture group whereas numerous colonies were apparent in the untreated control group.

With reference to FIGS. 21A to 21D, the predation of *A. baumannii* and *K. pneumoniae* by *B. bacteriovorus* was further examined, which resulted in ~3 log$_{10}$ reductions for both strains after 48 h. Looking at their concentration profiles, considerable differences between the two strains may be observed. While the amount of *A. baumannii* bacteria drastically decreased during the first 24 h (FIGS. 21A & B), *K. pneumoniae* group only showed significant decrease at the second day (from 24 to 48 h; FIGS. 21C & D). The differences in outer membrane structure and natural adaptation of the two pathogenic microbes may contribute to the lower lethality rate against *K. pneumoniae*.

Figure 22:
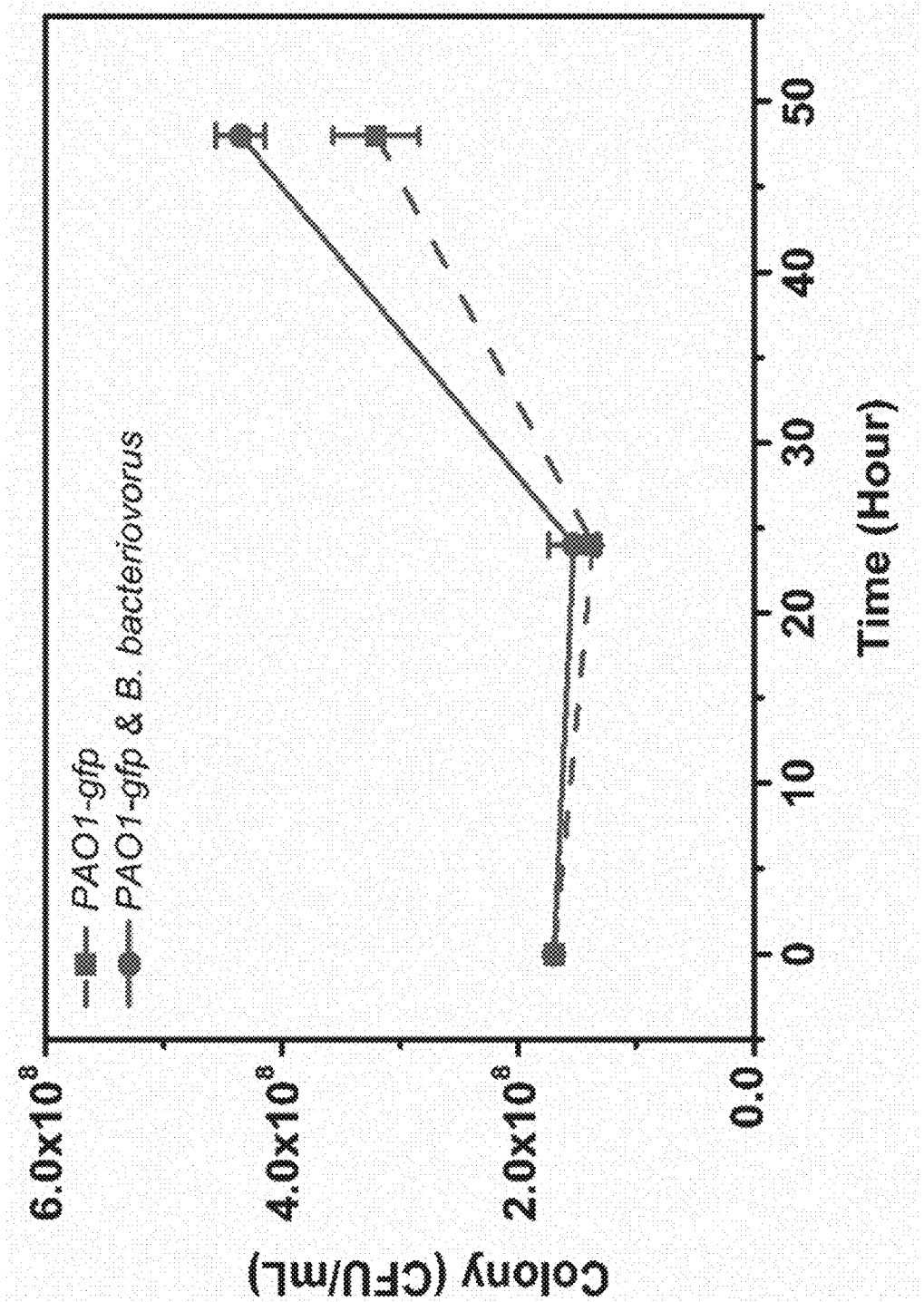
FIG. 22 is a plot showing in vitro predation effect of *B. bacteriovorus* delivered by cryoMNs against PAO1-gfp.

With reference to FIG. 22, compared to the significant predation efficiency for the above three bacteria, no predation was observed for PAO1-GFP bacteria. Colony counting revealed that both untreated PAO1-GFP and predated PAO1-GFP groups significantly increased on the second day, following the minor decrease in the first 24 h. It was reported previously that *B. bacteriovorus* may not be able to consume all gram-negative strains. For example, certain *B. bacteriovorus* can only prey upon selective *P. aeruginosa* strains such as Pa16, while in some other examples, only 70% of the tested *P. aeruginosa* strains were predated by *B. bacteriovorus* 109J strain. Meanwhile, *B. bacteriovorus* HD100 strain were able to prey upon all of the tested *P. aeruginosa* strains. Therefore, careful selection of the predatory strain may be performed to ensure efficacious predation towards pathogens.

Figure 23A:
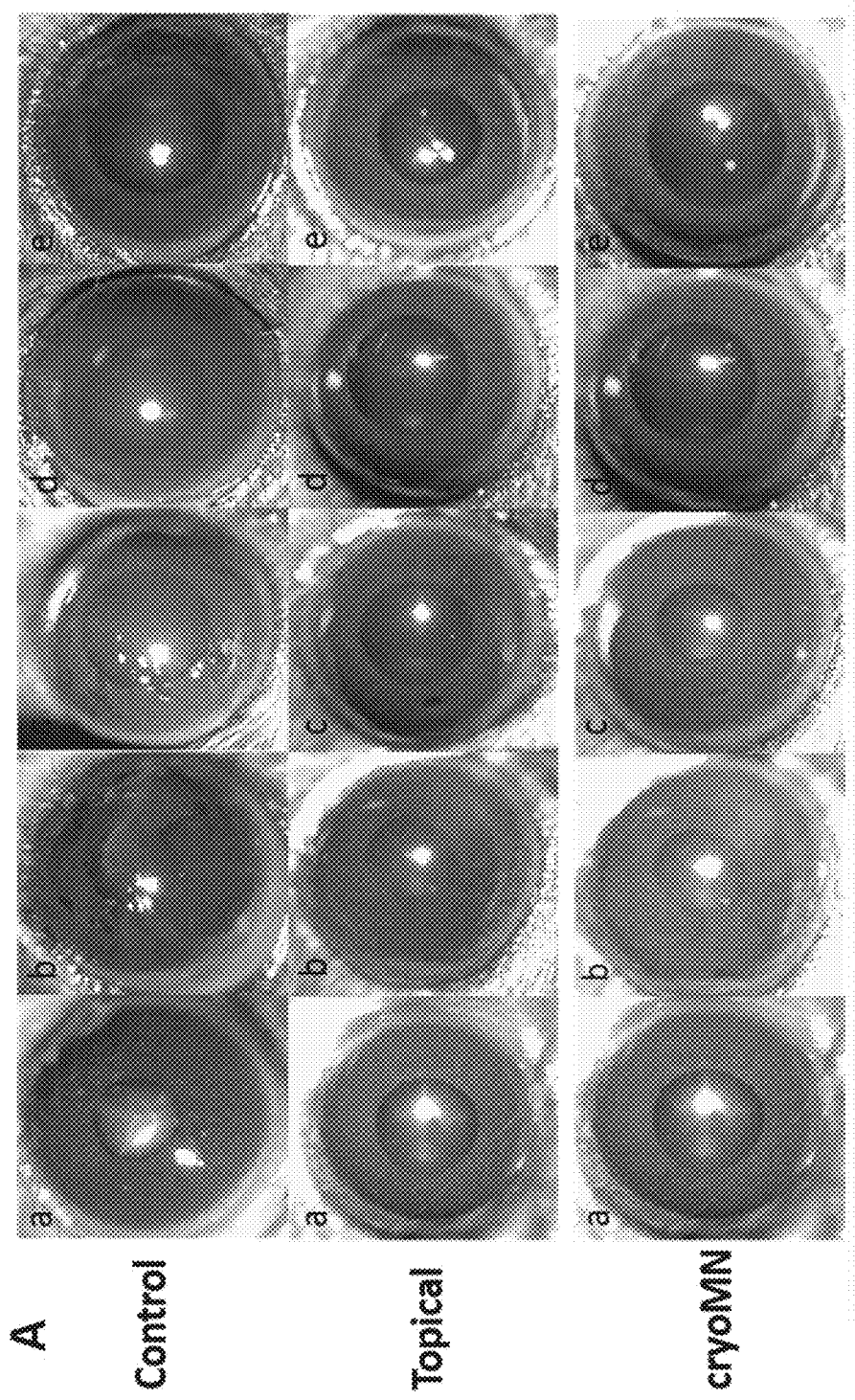

With reference to FIGS. 23A to 23C, there is shown an experiment on ocular delivery of *B. bacteriovorus* with cryoMNs for eye infection.

To evaluate cryoMN therapy efficacy in an in vivo setting, treatment was conducted in a mice model of infectious keratitis. At 6 h post inoculation of *E. coli* (ATCC25922) of scarified cornea, clear signs of infection in terms of corneal haze could be observed by slit-lamp bioimaging, as shown in FIG. 23A. The images indicated significant opacity around the pupillary area. To this end, treatment was conducted twice with 3 h gap in the first day, and thrice (3 h gap) for the second and third day. The eyes were examined by slit lamp and OCT prior to each treatment and the mice were sacrificed at day 4 to isolate and quantify the bacteria in cornea. With increasing time, sham control progressed towards enhanced corneal haze and stromal infiltrates whereas cornea that received treatment with predatory bacteria appeared clear or slight opacity around pupil area. In support of these observations, bacterial bioburden in cornea determined by bacterial enumeration indicated marked decrease in bacterial titer for both topically applied as well as MN application.

These results indicated predation efficiency of *B. bacteriovorus* in vivo, as shown in FIG. 23B. Notably, *E. coli* concentration was lowest in the cryoMN group, 5.8-fold lower relative to the control group, and 2.6-fold lower to the topical group. Cornea thickness was evaluated daily before each treatment. Interestingly, the topical group showed comparable results with the control group and cryoMN group in FIG. 23C.

Advantageously, a novel MN patch formulation (cryoMNs) to deliver living microbial for the treatment of ocular infections is provided. This formulation consists of mainly two major components, namely the cryoprotectant medium and the live therapeutics—predators (i.e. *B. bacteriovorus*). The cryoprotectant medium maintains the survival and activity of the predators in their native form during the preparation, storage, and deployment. 5% glycerol was found to be the optimized medium, providing sufficient mechanical strength and integrity, while retaining the viability of *B. bacteriovorus* greater than 80%. *B. bacteriovorus* was chosen as the model predator here due to its unique capability for predating gram-negative bacteria.

In addition, the activation of *B. bacteriovorus* after the deployment of cryoMN patch is rapid (within 80 s) and they are then able to prey the bacteria within 18 to 24 h, minimizing the time lag and saving the initiation time significantly. As shown in the earlier described experimentation results, both CFU plating and optical density method confirmed that the predation capability of *B. bacteriovorus* was fully retained in the cryoMN formulation. Additional testing with *A. baumannii* and *K. pneumoniae* revealed the potential treatment of keratitis and endophthalmitis, respectively using cryoMNs carrying *B. bacteriovorus*. However, *B. bacteriovorus* did not effectively prey on PAO1-GFP strains, indicating the necessary pre-identification of the pathogen strains before the treatment. Finally, the mouse eye infection model demonstrates the clinical potentials of this technology. Compared with the topical delivery of *B. bacteriovorus*, cryoMN-aided delivery significantly improved the effectiveness of the treatment.

In cell experiments, the predatory bacteria (*B. bacteriovorus*) delivered with this device successfully suppressed the proliferation of the gram-negative *E. coli, A. baumannii* and *K. pneumoniae*. In the mouse eye infection model, the *B. bacteriovorus* delivered via cryoMN significantly reduced the *E. coli* concentration in the cornea relative to control or topical treatment. The embodiments of the present invention are versatile and can be expanded to other predators to prey on specific target pathogens.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A cryo formulation-based microneedle device for ocular delivery of bioactive therapeutic agents, comprising:
   one or more microneedle patches each including an array of miniaturized needles, each miniaturized needle defining a base end and a tip; and
   a substrate to which the base end of each miniaturized needle of the array of miniaturized needles is attached or integrated thereto;
   wherein the one or more microneedle patches are in a cryo status;
   wherein each of the one or more microneedle patches are adapted to be applied on a cornea of an eye, in which the miniaturized needles penetrate into the eye;
   wherein each of the one or more microneedle patches comprises a matrix solution, wherein the matrix solution comprises an aqueous base material excluding water, saline, phosphate-buffered saline (PBS) and HEPES, and at least one cryoprotectant excluding DMSO, ethylene glycol, trehalose, dextrose, PEG, PVP, PVA, HA, gelatin, agarose, alginate, chitosan, cellulose, collagen, chitin, heparin and mucin;
   wherein the miniaturized needles are further arranged to melt so as to release one or more bioactive therapeutic agents into the eye to achieve a targeted therapeutic effect; and
   wherein the one or more bioactive therapeutic agents comprise predatory bacteria.

2. The microneedle device according to claim 1, wherein each of the one or more microneedle patches consists of the matrix solution and the one or more bioactive therapeutic agents.

3. The microneedle device according to claim 2, wherein the one or more bioactive therapeutic agents further comprises a plurality of biological cells including at least one of cancer cells, fibroblasts, endothelial cells, smooth muscle cells, stem cells, melanocytes, dendritic cells, neutrophils, and T-cells.

4. The microneedle device according to claim 2, wherein the one or more bioactive therapeutic agents further comprises a biochemical substance including at least one of drugs, vaccines, proteins, peptides, nucleic acids, virus and fungi.

5. A method of fabricating a microneedle device in accordance with claim 2, comprising the steps of:
   casting the matrix solution containing the one or more bioactive therapeutic agents into a mold defined with an array of miniaturized needles;
   freezing the matrix solution to define the array of miniaturized needles on one of the one or more microneedle patches; and
   detaching the one or more microneedle patches from the mold.

6. The method according to claim 5, wherein the mold includes a PDMS mold or a metal mold.

7. The method according to claim 5, further comprising the step of urging the bioactive therapeutic agents and/or the matrix solution into the array of microneedle structures define on the mold.

8. The method according to claim 7, wherein the one or more bioactive therapeutic agents and/or the matrix solution are urged into the mold using centrifugation or sedimentation.

9. The method according to claim 7, further comprising the step of storing the one or more microneedle patches at below −80° C.

10. The method according to claim 5, wherein the mold is a PDMS mold, the method further comprising the step of fabricating the PDMS mold using a metal mold, wherein the PDMS mold is a negative mold and the metal mold is a positive template defined with a predetermined pattern of the array of microneedle structures.

11. The microneedle device according to claim 1, wherein the one or more bioactive therapeutic agents comprise *Bdellovibrio Bacteriovorus*.

12. The microneedle device according to claim 1, wherein the targeted therapeutic effect includes eye infection treatment.

13. The cryo formulation-based microneedle device for ocular delivery of bioactive therapeutic agents as claimed in claim 1, wherein the aqueous base solution comprises glycerol.

14. The cryo formulation-based microneedle device for ocular delivery of bioactive therapeutic agents as claimed in claim 1, wherein the cryoprotectant includes at least one of glycerol, sucrose, fructose, galactose, and proteins.

15. The cryo formulation-based microneedle device for ocular delivery of bioactive therapeutic agents as claimed in claim 1, wherein the cryoprotectant includes at least one of poly-l-lysine, starch, carboxymethyl cellulose (CMC), dextran, guar gum, pullulan, xanthan, xyloglucan, chondroitin, keratan, and their derivatives thereof.

16. A method of using the microneedle device in accordance with claim 1, comprising the step of:
   removing the microneedle device from a storage place; and
   applying the microneedle device within a predetermined period of time after removal from the storage place.

17. The method of claim 16, wherein the predetermined period of time is 30 seconds.

18. The method of claim 16, wherein the one or more microneedle patches are arranged to facilitate a predetermined penetration depth of the one or more bioactive therapeutic agents into the eye.

19. The method of claim 18, wherein the predetermined penetration depth is 50-1000 μm.

20. The method of claim 16, further comprising the step of temporally attaching the microneedle device to a handle, thereby allowing an operator to apply the microneedle device by holding the handle.

21. A cryo formulation-based microneedle device for ocular delivery of bioactive therapeutic agents, comprising:
   one or more microneedle patches each including an array of miniaturized needles, each miniaturized needle defining a base end and a tip; and
   a substrate to which the base end of each miniaturized needle of the array of miniaturized needles is attached or integrated thereto;
   wherein the one or more microneedle patches are in a cryo status;
   wherein each of the one or more microneedle patches is adapted to be applied on a cornea of an eye, in which the miniaturized needles penetrate into the eye;
   wherein each of the one or more microneedle patches comprises a matrix solution, wherein the matrix solution comprises an aqueous base material and at least one cryoprotectant, the aqueous base solution includes glycerol, the cryoprotectant includes at least one of glycerol, sucrose, fructose, galactose, proteins, poly-l-lysine, starch, carboxymethyl cellulose (CMC), dextran, guar gum, pullulan, xanthan, xyloglucan, chondroitin, keratin and their derivatives thereof; and wherein the miniaturized needles are further arranged to melt so as to release one or more bioactive therapeutic agents into the eye to achieve a targeted therapeutic effect.

22. The cryo formulation-based microneedle device for ocular delivery of bioactive therapeutic agents according to claim 21, wherein each of the one or more microneedle patches consists of the matrix solution and the one or more bioactive therapeutic agents.

23. The cryo formulation-based microneedle device for ocular delivery of bioactive therapeutic agents according to claim 22, wherein the one or more bioactive therapeutic agents comprise a plurality of biological cells including at least one of cancer cells, fibroblasts, endothelial cells, smooth muscle cells, stem cells, melanocytes, dendritic cells, neutrophils, and T-cells.

24. The cryo formulation-based microneedle device for ocular delivery of bioactive therapeutic agents according to claim 22, wherein the one or more bioactive therapeutic agents comprise a biochemical substance including at least one of drugs, vaccines, proteins, peptides, nucleic acids, virus and fungi.

25. The cryo formulation-based microneedle device for ocular delivery of bioactive therapeutic agents according to claim 22, wherein the one or more bioactive therapeutic agents comprise bacteria.

26. The cryo formulation-based microneedle device for ocular delivery of bioactive therapeutic agents according to claim 25, wherein the one or more bioactive therapeutic agents comprise predatory bacteria.

27. The cryo formulation-based microneedle device for ocular delivery of bioactive therapeutic agents according to claim 26, wherein the one or more bioactive therapeutic agents comprise *Bdellovibrio Bacteriovorus*.

28. The cryo formulation-based microneedle device for ocular delivery of bioactive therapeutic agents according to claim 25, wherein the targeted therapeutic effect includes eye infection treatment.

29. A cryo formulation-based microneedle device for ocular delivery of bioactive therapeutic agents, comprising:
one or more microneedle patches each including an array of miniaturized needles, each miniaturized needle defining a base end and a tip; and
a substrate to which the base end of each miniaturized needle of the array of miniaturized needles is attached or integrated thereto;
wherein the one or more microneedle patches are in a cryo status;
wherein each of the one or more microneedle patches is adapted to be applied on a cornea of an eye, in which the miniaturized needles penetrate into the eye;
wherein each of the one or more microneedle patches comprises a matrix solution, wherein the matrix solution comprises glycerol, and wherein the amount of glycerol is from 1 to 5 wt. % of the matrix solution; and
wherein the miniaturized needles are further arranged to melt so as to release one or more bioactive therapeutic agents into the eye to achieve a targeted therapeutic effect; and
wherein the one or more bioactive therapeutic agents comprise predatory bacteria.

30. The cryo formulation-based microneedle device for ocular delivery of bioactive therapeutic agents according to claim 29, wherein each of the one or more microneedle patches consists of the matrix solution and the one or more bioactive therapeutic agents.

31. The cryo formulation-based microneedle device for ocular delivery of bioactive therapeutic agents according to claim 30, wherein the one or more bioactive therapeutic agents comprise a plurality of biological cells including at least one of cancer cells, fibroblasts, endothelial cells, smooth muscle cells, stem cells, melanocytes, dendritic cells, neutrophils, and T-cells.

32. The cryo formulation-based microneedle device for ocular delivery of bioactive therapeutic agents according to claim 30, wherein the one or more bioactive therapeutic agents comprise a biochemical substance including at least one of drugs, vaccines, proteins, peptides, nucleic acids, virus and fungi.

33. The cryo formulation-based microneedle device for ocular delivery of bioactive therapeutic agents according to claim 29, wherein the one or more bioactive therapeutic agents comprise *Bdellovibrio Bacteriovorus*.

34. The cryo formulation-based microneedle device for ocular delivery of bioactive therapeutic agents according to claim 29, wherein the targeted therapeutic effect includes eye infection treatment.

35. The cryo formulation-based microneedle device for ocular delivery of bioactive therapeutic agents according to claim 29, wherein the matrix solution consists of an aqueous base solution and a cryoprotectant.

36. The cryo formulation-based microneedle device for ocular delivery of bioactive therapeutic agents as claimed in claim 35, wherein the aqueous base solution comprises at least one of water, phosphate-buffered saline (PBS) and 4-(2-hydroxyethyl)-1-piperazineethanesulfonic acid (HEPES).

37. The cryo formulation-based microneedle device for ocular delivery of bioactive therapeutic agents as claimed in claim 35, wherein the cryoprotectant includes at least one of dimethyl sulfoxide (DMSO), ethylene glycol, sucrose, fructose, trehalose, galactose, dextrose and proteins.

38. The cryo formulation-based microneedle device for ocular delivery of bioactive therapeutic agents as claimed in claim 35, wherein the cryoprotectant includes at least one of poly(ethylene glycol) (PEG), polyvinylpyrrolidone (PVP), polyvinyl alcohol (PVA), poly-l-lysine, hyaluronic acid (HA), starch, gelatin, agarose, alginate, chitosan, cellulose, carboxymethyl cellulose (CMC), collagen, chitin, dextran, guar gum, pullulan, xanthan, xyloglucan, heparin, chondroitin, keratan, mucin, and their derivatives thereof.

* * * * *